United States Patent [19]
Bledsoe et al.

[11] Patent Number: 5,406,955
[45] Date of Patent: Apr. 18, 1995

[54] ECG RECORDER AND PLAYBACK UNIT

[75] Inventors: J. Daren Bledsoe; David L. Burton, both of McMinnville, Oreg.; Brian C. Dunn, Brentwood, Calif.; Brian D. Setterberg, McMinnville, Oreg.; Dennis E. Ochs, McMinnville, Oreg.; David E. Smith, Wilsonville, Oreg.; Edward L. Feldhousen, Tualatin, Oreg.; Howard E. Hilton, Snohomish, Wash.

[73] Assignee: Hewlett-Packard Corporation, Palo Alto, Calif.

[21] Appl. No.: 31,437

[22] Filed: Mar. 12, 1993

[51] Int. Cl.⁶ .......................................... A61B 5/0432
[52] U.S. Cl. .................................................. 128/711
[58] Field of Search ........................ 128/696, 710, 711

[56] References Cited

U.S. PATENT DOCUMENTS

| | | | |
|---|---|---|---|
| 4,098,267 | 7/1978 | Stein et al. | |
| 4,291,703 | 9/1981 | Kelen | 128/711 |
| 4,333,475 | 6/1982 | Moreno et al. | 128/711 |
| 4,422,459 | 12/1983 | Simson | 128/702 |
| 4,457,315 | 7/1984 | Bennish | 128/704 |
| 4,532,934 | 8/1985 | Kelen | 128/697 |
| 4,565,201 | 1/1986 | Lass | 128/696 |
| 4,624,263 | 11/1986 | Slavin | 128/710 |
| 4,630,204 | 12/1986 | Mortara | 364/417 |
| 4,680,708 | 7/1987 | Ambos et al. | 364/417 |
| 4,696,306 | 9/1987 | Shiozaki | 128/711 |
| 4,721,114 | 1/1988 | DeFault et al. | 128/696 |
| 4,883,065 | 11/1989 | Kelen | 128/711 |
| 4,961,428 | 10/1990 | Nikias et al. | 128/699 |
| 5,030,911 | 7/1991 | Lam | 324/226 |
| 5,050,021 | 9/1991 | Shu et al. | 360/95 |

OTHER PUBLICATIONS

Oppenheim And Schafer, Digital Signal Processing, 1975, p. 19.
Service Manual For Holter Acquisition Module, "Preliminary", Marquette Electronics Inc., Jun. 15, 1993, pp. 9-11.
Jorgensen, The Complete Handbook, Magnetic Recording, 3rd Edition 1998, pp. 492-497.
Woram, The Recording Studio Handbook, 1980, p. 279.
Setterberg, Brian, *An Analysis of the Marquette Electronics, Inc.*

*Primary Examiner*—William E. Kamm
*Attorney, Agent, or Firm*—Curtis G. Rose

[57] ABSTRACT

An ECG recorder and playback unit which includes software-implemented digital signal processing filters which compensate for phase and magnitude distortion occurring when an ECG signal is recorded on a Holter recorder and played back. This permits "tuning" a recorder and playback unit which may be unrelated, as when made by different manufacturers. An impulse or step signal is recorded and played back to provide a system frequency response measurement. Coefficients for a digital correction filter are derived from the discrete Fourier transform of the impulse or step response and a desired system response. When recorded ECG data is played back, it is filtered on a substantially real-time basis with the digital correction filter to compensate for phase and magnitude distortion. Prior to recording, the high frequencies of the ECG signal are boosted to compensate for high frequency losses inherent in the recording and playing back of ECG signals. A calibration pulse and a system characterization pulse are derived by statistically selecting from a plurality of pulses and averaging the selected pulses in order to minimize the effects of noise and tape defects in the pulses. High frequency components of the ECG signal can be amplified prior to recording the signal. This results in decreased amplification, and therefore noise, when the recorded signals are played back. Cardiac pacer pulse detection is performed prior to the step of filtering the played back signal to optimize pulse detection.

33 Claims, 32 Drawing Sheets

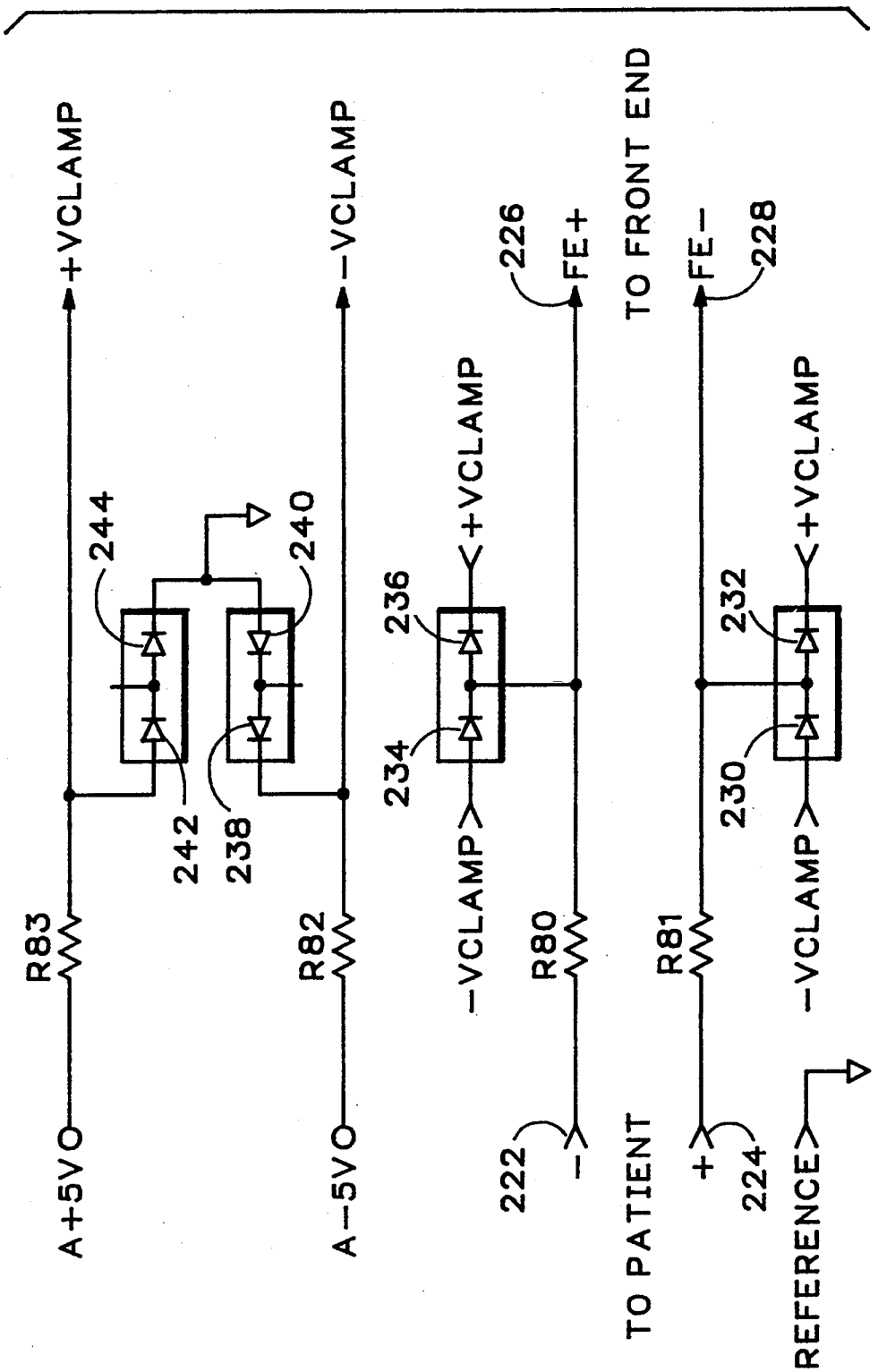

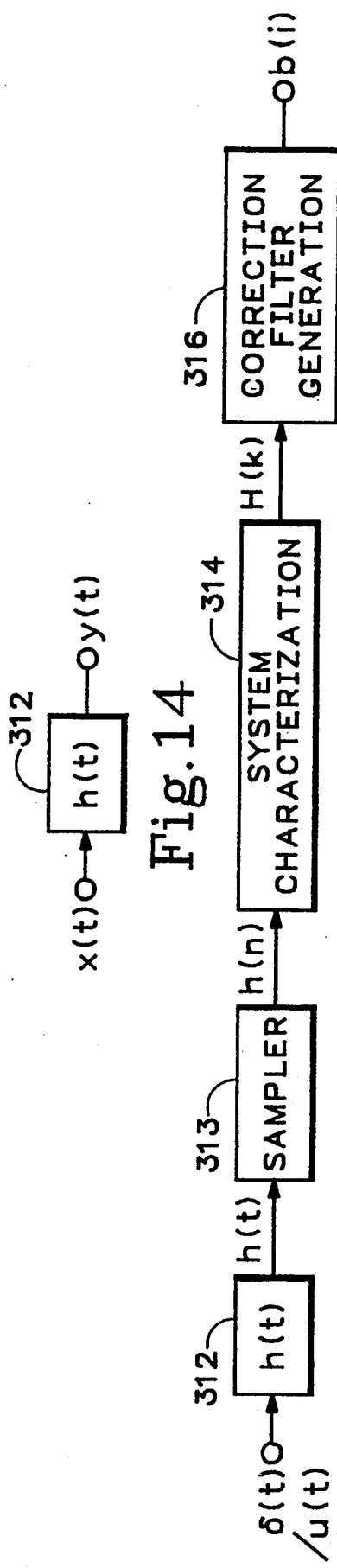
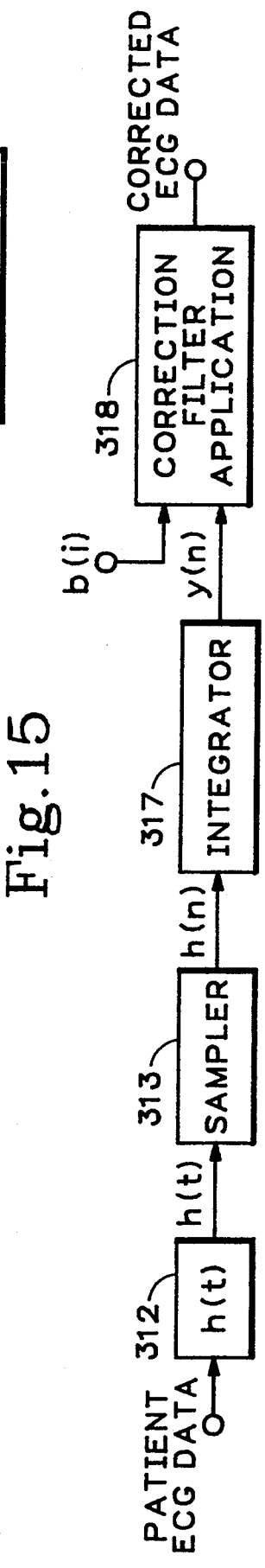
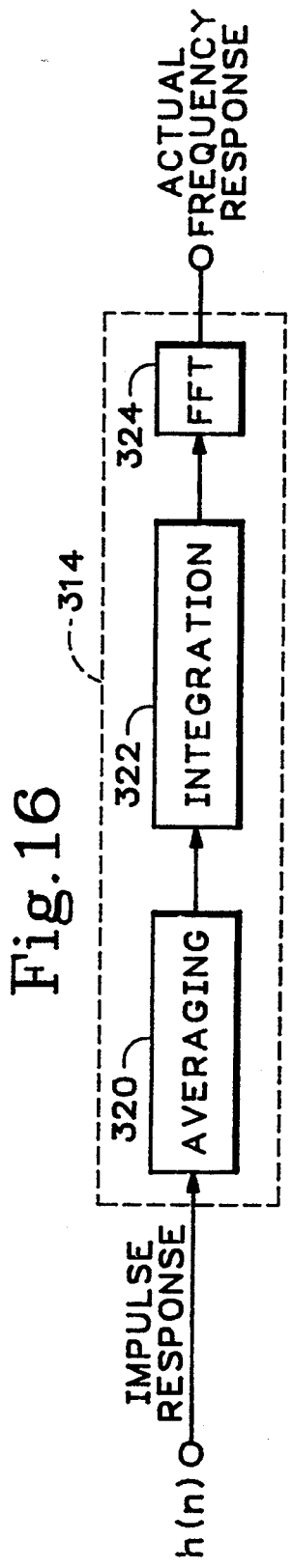
Fig. 14
Fig. 15
Fig. 16
Fig. 17

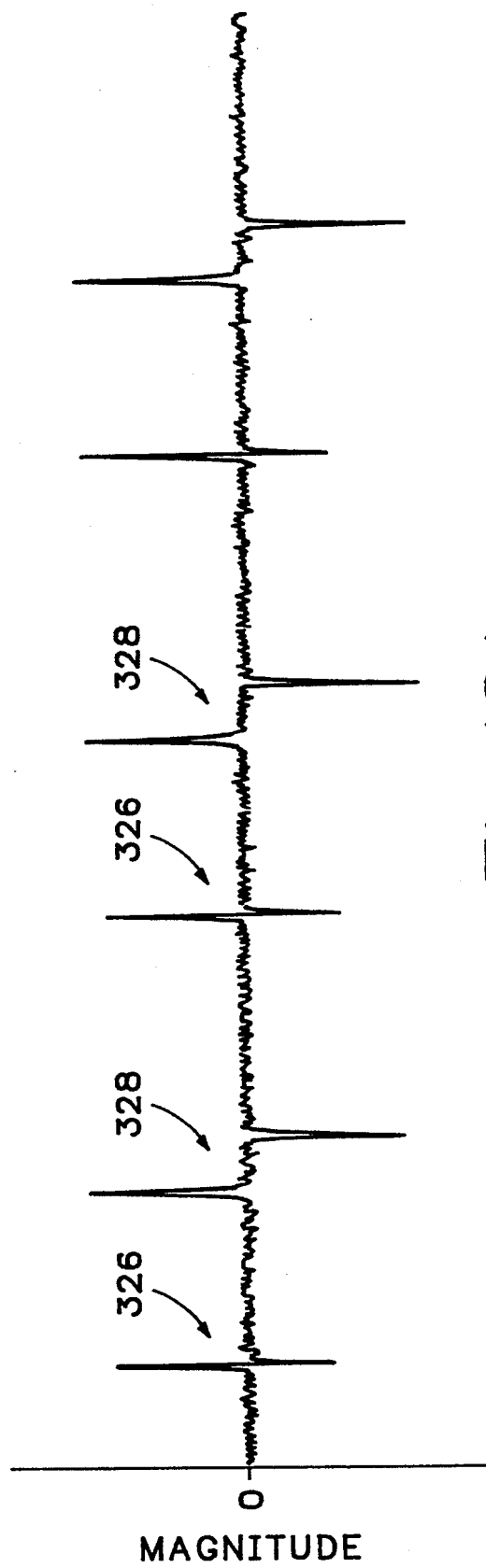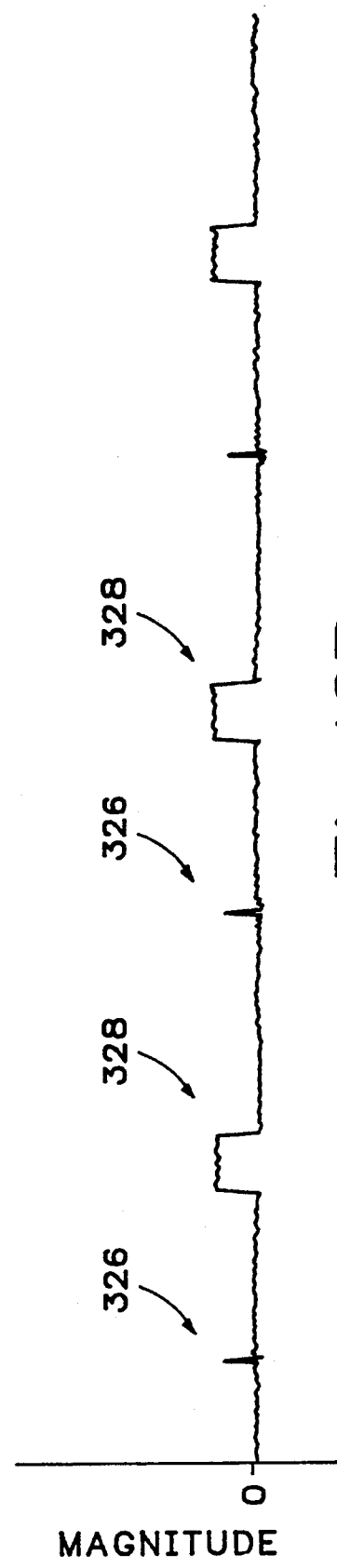

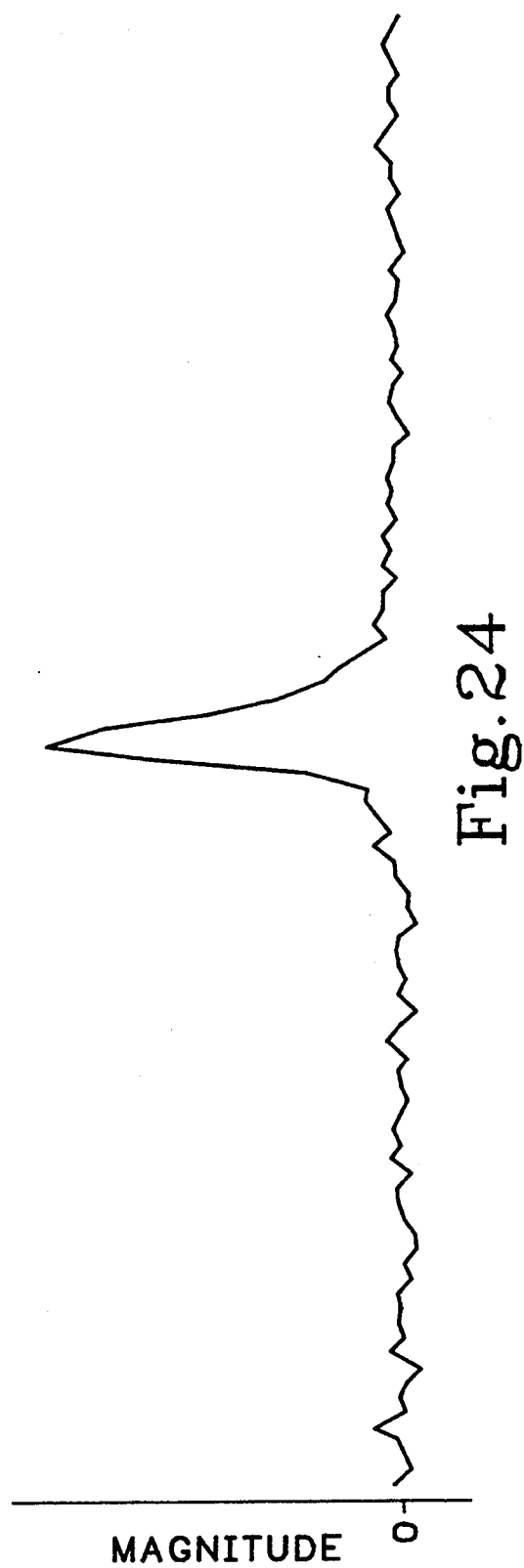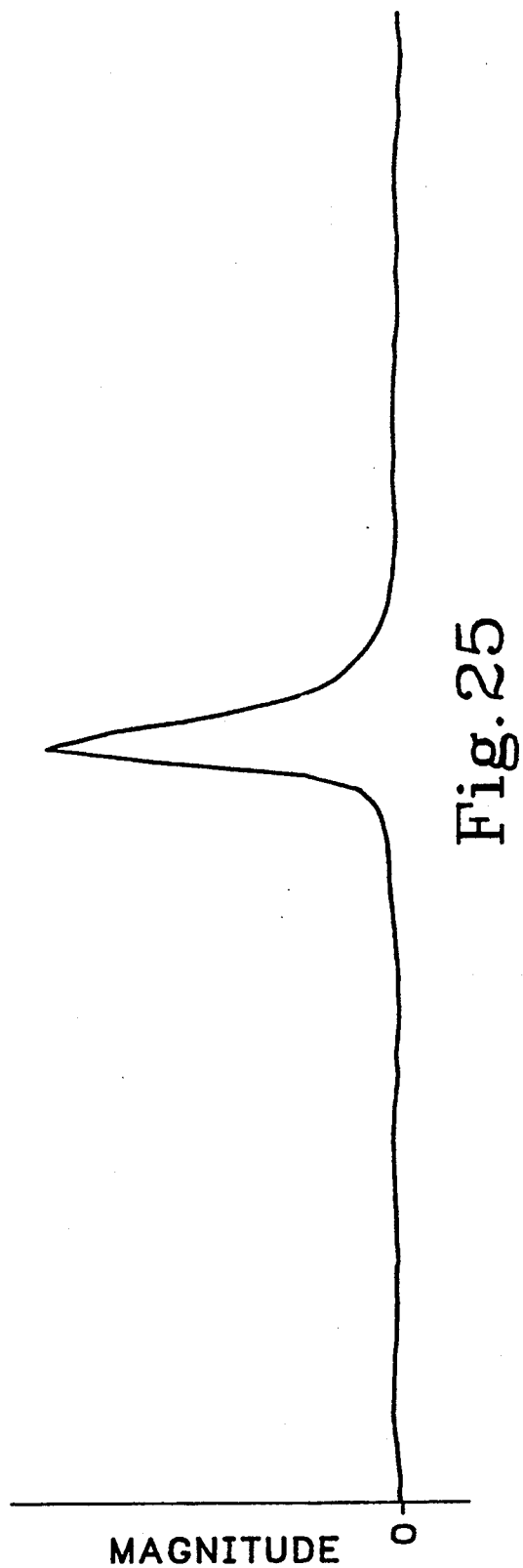

ECG RECORDER AND PLAYBACK UNIT

BACKGROUND OF THE INVENTION

1. Field of the Invention

The present invention relates to methods and apparatus for recording and playing back ECG signals and more particularly to such methods and apparatus in which the ECG signals are processed to remove phase and magnitude distortion occurring during the recording and playback process.

2. Description of the Related Art

Prior art systems, known as Holter recorders, record ECG signals which are provided from a patient via electrodes to a small recorder carried by the patient. The EGG signals are continuously recorded on an analog tape typically over a 24 hour period. Several prior art systems use a conventional C60 analog cassette tape of the type typically used to record audio information. In order to do so, the tape must be slowed down approximately 50 times from normal audio speeds. Usually three channels of EGG data are recorded plus a fourth channel which includes a timing signal that is generated by the recorder.

After recording, the tape is played back on a device which runs the tape at high speed and processes the analog signals derived from the tape. Such processing typically includes analog filters which are intended to compensate for dropoff at both the low and high frequencies and for phase distortion which results from the magnetic recording and playback process. The filtered signals are digitized and further processed into a report for analysis by a physician.

As used herein, the term magnitude response refers to the manner in which a system for recording and playing back an ECG signal affects the magnitude of a signal as the signal frequency varies. The term phase response refers to the manner in which such a system affects the phase of a signal as the signal frequency varies. Magnitude response and phase response are referred to herein collectively as frequency response. An ideal system for recording and playing back EGG signals would have a substantially flat magnitude response and a linear phase response. Analog tape recording technology of the type described above suffers from several limitations which adversely affect both the magnitude and the phase response of prior art systems for recording and playing back ECG signals. Because the playback head on a device for scanning (i.e., playing back) recorded ECG signals detects only the rate of change of tape flux, there is no magnitude response at DC. The playback head in essence differentiates signals on the tape. This differentiation has the effect of phase shifting signals positive 90 degrees and attenuating low frequency signals. To recover the original information, the playback unit must integrate the output signal from the playback head. This integration process compensates for the differentiation by providing negative 90 degrees phase shift and amplification of low frequencies. In prior art systems, the integration process results in phase distortion and excessive amplification of low frequency noise (baseline wander).

High frequency magnitude response of the playback signal tends to drop off due to the physical limits of the playback head, recording head inductance, tape coating effects and also as a result of the slow rate of tape transport during recording. This effect may be compensated for by boosting the played back signal in the high frequencies. This has the effect of increasing both signal and noise in this range. Recent research indicates that there is clinically important information which can be obtained from an ECG signal above 40 Hz; increased noise in this range is therefore undesirable.

As mentioned above, prior art systems filter the signal derived from a tape playback head during scanning of the recorded tape in an effort to compensate for phase and magnitude distortion. Such systems suffer from several disadvantages. First, analog filters are not as accurately implemented as a digital filter due to variations in component tolerance. In addition, analog filters are subject to drift. More importantly, prior art analog filters are relatively fixed in the manner in which they compensate. In other words, a fixed phase and magnitude distortion is assumed in the system for recording and playing back the signal. An analog filter is designed which compensates for the assumed distortion. One problem with this approach is that phase and magnitude distortion produced by a system for recording and playing back ECG signals varies over time. It can vary as a result of wear on the heads for recording and playing back the signal. It can also vary in response to misalignment of the mechanical components which affect the record and playback head compliance with the tape. If the recorder is not matched with the playback unit, e.g., if they are made by different manufacturers, the filter may not compensate properly. Different recorders will therefore produce different results when the recorded data is played back on the same playback unit. Independently of time, distortion can vary as a result, e.g., of using an analog tape having a different thickness or type of tape coating thereon.

Prior art techniques for calibrating the ECG recorder include recording a series of rectangular calibration pulses of known amplitude on each of three channels used for recording ECG signals. Pulses are played back through a playback deck and passed through analog compensation filters to restore the pulse's original phase and frequency content. The playback unit is calibrated by measuring the amplitude of the calibration pulses and thereafter generating a data scaler which is applied to the ECG data.

There are several problems with this approach. One is that phase and magnitude distortion can vary from channel to channel. Also, generating a data scaler does not compensate phase and magnitude over frequency. Another problem results from a phenomenon called tape dropout. Tape dropout is an apparent reduced recording level on a tape caused by variations in the recording medium. When such areas are encountered during the calibration process, accuracy of calibration is adversely affected.

SUMMARY OF THE INVENTION

The present invention provides a method and apparatus for processing ECG data which is collected by a system for recording and playing back the data. In performing the method, a system frequency response is measured. Then, a correction filter response is derived from the system frequency response and a predetermined desired frequency response. ECG data is recorded and played back using the system. The played-back ECG data is filtered with the correction filter response. In another aspect of the invention, the filtering is done using digital signal processing techniques on a substantially real-time basis by digitizing the data, dividing the digitized data into predetermined block sizes and thereafter forward and reverse filtering each block of data.

In another aspect of the invention, high frequency components of the ECG signal are boosted prior to recording the same on an analog tape. This pre-emphasis scheme compensates for the losses of the recording and playback processes without requiring increased gain in amplifiers for the played-back signal which also amplify noise inherent in the playback amplifiers and magnetic tape.

In another aspect of the invention, calibration pulses are statistically selected and averaged in order to reduce the effects of noise and tape dropout on the calibration process.

In another aspect of the invention, cardiac pacer pulses are detected prior to filtering the recorded EGG signals to compensate for magnitude and phase distortion. The accuracy and ease of pacer pulse detection is improved when done on differentiated data prior to filtering.

In another aspect, a characteristic such as frequency response or time base error, is measured. An acceptable range for the measurement is defined and a system operator is alerted when the measurement falls outside of the range.

It is a general object of the present invention to provide an ECG recorder and playback unit and method which overcomes the above-enumerated disadvantages associated with prior art systems and methods.

It is another object of the present invention to compensate played-back EGG signals for phase and magnitude distortion occurring as a result of the recording and playback process.

It is another object of the present invention to compensate for such distortion utilizing digital signal processing techniques on a substantially real-time basis.

It is another object of the present invention to boost the high frequencies of the EGG signal prior to recording the signal.

It is another object of the present invention to generate an averaged input characterization pulse for determining a system transfer function that is used to derive a correction filter response.

It is another object of the present invention to generate an average calibration pulse to improve system calibration.

It is another object of the present invention to detect cardiac pacer pulses prior to ECG signal compensation filtering.

It is another object of the present invention to verify system performance for each procedure.

It is another object of the present invention to provide adaptable filter parameters and to permit either selective or automatic reconfiguration of filter parameters.

It is another object of the present invention to permit using recorders which are not matched with the playback unit and which may even be made by different manufacturers.

It is another object of the present invention to permit a user to set or adjust the low and high frequency system response.

It is another object of the present invention to minimize baseline wander while preserving low frequency phase of the played back ECG signal.

The foregoing and other objects, features and advantages of the invention will become more readily apparent from the following detailed description of a preferred embodiment which proceeds with reference to the drawings.

BRIEF DESCRIPTION OF THE DRAWINGS

FIG. 5AA is a block diagram of another embodiment of a calibration pulse generator.

FIG. 5C is a schematic of a defibrillator protection circuit contained in the block diagram of FIG. 5A.

FIG. 14 is a block diagram of a recorder and playback unit modeled as a black box transfer function.

FIG. 15 is a block diagram illustrating a process for characterizing the frequency response of the recorder and playback unit and for generating a correction filter response.

FIG. 16 is a block diagram illustrating a process for applying a correction filter to played-back patient ECG data.

FIG. 17 is a detailed block diagram of system characterization block 314 of FIG. 15.

FIG. 18A is an illustration of a differentiated impulse response signal interleaved with a calibration pulse signal.

FIG. 18B is an illustration of the signal in FIG. 18A after integration.

FIG. 24 is an illustration of a "noisy" impulse response.

FIG. 25 is an illustration of an averaged impulse response after averaging 148 impulses.

DETAILED DESCRIPTION OF THE PREFERRED EMBODIMENT

Figure 1:
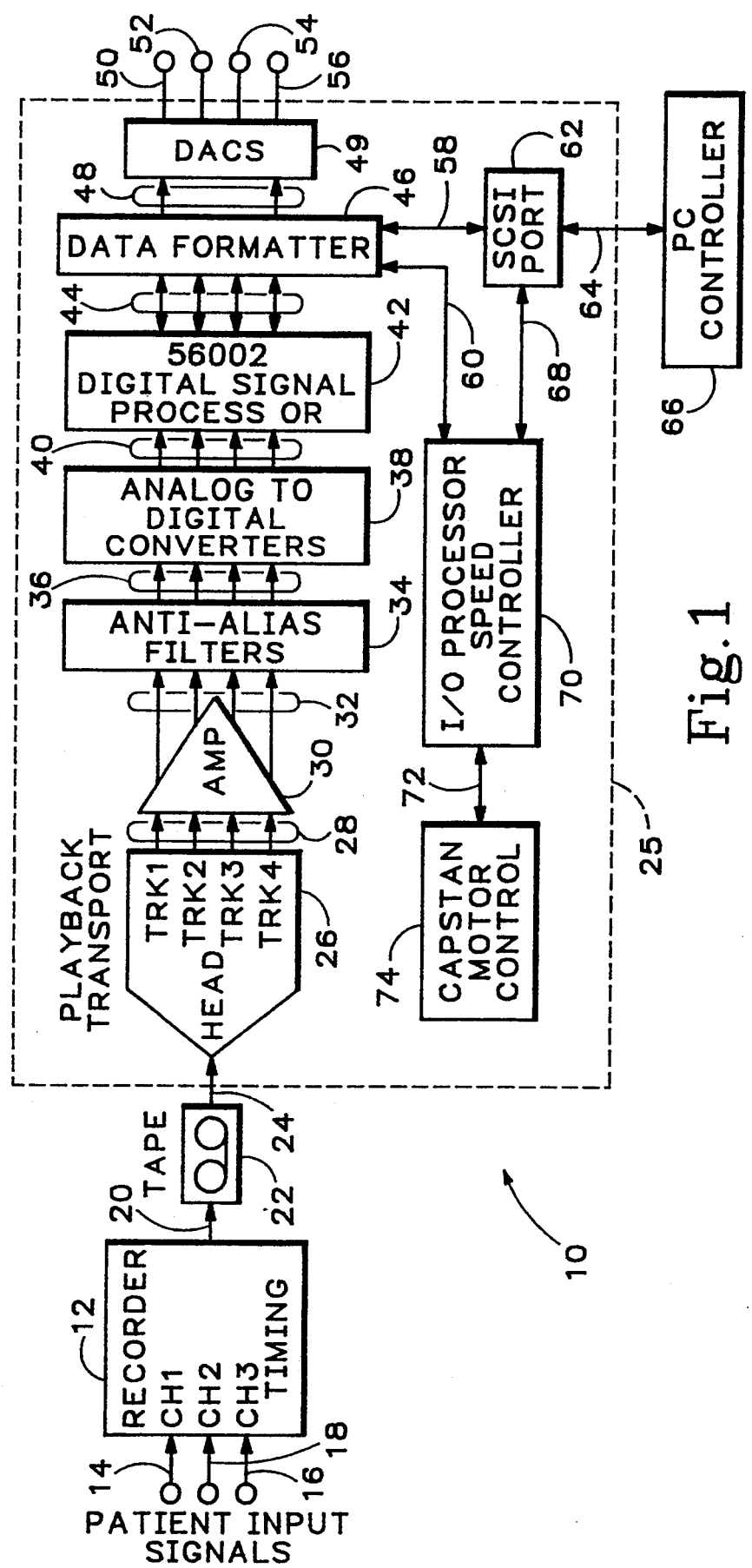
FIG. 1 is block diagram of a Holter recorder and playback unit.

Referring to FIG. 1, a Holter recorder and playback unit is shown generally at 10. The system comprises a portable Holter recorder 12 for recording ECG patient signals received over patient monitor lines 14, 16, and 18, which are typically connected to patch-type electrodes affixed to the patient's skin. A different ECG signal is provided on each of the three lines. Recorder 12 is desirably a miniature recorder worn on the patient's belt in order to collect data over an extended period of time. The portable Holter recorder 12 also includes means for generating and recording a repetitive characterization signal (not shown in FIG. 1 and explained in greater detail below).

The ECG patient signals and characterization signal are processed within recorder 12 to produce recorder signals 20 capable of being stored on a standard magnetic cassette tape 22 held in the recorder 12. Each of the three ECG signals is recorded onto separate tracks of the magnetic cassette tape 22, e.g., tracks 1, 2 and 4. As will be described shortly, a characterization signal may also be recorded on the tape tracks prior to recording the ECG signals. A timing signal is recorded onto yet another separate, track 3. The timing signal is a constant frequency signal which creates timing information on tape 22. In addition, a patient activated signal, created by depressing a switch, can be captured on the timing track.

After ECG signals are recorded on tape 22, it is removed from recorder 12 and installed in a playback transport system 25. Each of the four recorded tracks are played back by playback unit 25 which includes a playback transport and post processing circuitry, as well as computer control interface and testing outputs. A playback head 26 converts the information stored on each of the four tracks on magnetic tape 22 into four separate analog playback signals which are applied to analog track lines 28. Each track line corresponds to one of four separate tracks on the tape 22. The circuitry contained in each of blocks 30, 34, 38, and 42, described below, is replicated for each track although separate blocks for each channel are not shown in FIG. 1 to simplify the drawing. Although the preferred embodiment shown in FIG. 1 uses a four track tape, any reasonable number of tracks and patient inputs can be used.

The analog track lines 28 are connected to playback amplifiers 30. The playback amplifiers 30 amplify the analog recorded signals on analog track lines 28 to produce amplified analog signals on amplifier output lines 32. The amplifier output lines 32 are connected to anti-alias filters 34 which act essentially as low pass filters having a corner frequency of about 200 kHz. In the preferred embodiment the anti-alias filters 34 are implemented using conventional R-C networks. The filtered analog signals produced by the anti-alias filters 34 are coupled to analog-to-digital converters ("ADCs") 38 over filter output lines 36 connected between the anti-alias filters 34 and ADCs 38. Analog-to-digital converters 38 also have anti-alias filters with a corner frequency of about 50 kHz.

The analog signals received by ADCs 38 are converted into a digital representation for subsequent digital processing by digital signal processors ("DSP") 42. In the preferred embodiment, each of the analog-to-digital converters is a 56ADC16 manufactured by Motorola of Phoenix, Ariz. The ADCs 38 produce digital outputs on busses 40 which are connected to digital signal processors 42. Each of the digital outputs is a 16-bit sample value which is applied to bus 40 at a rate of 100,000 samples/second. The digital signal processors 42 includes a separate signal processor dedicated to each track. Each of the digital signal processors, in the preferred embodiment, is a 56002 DSP also manufactured by Motorola. The digital signal processors perform the necessary digital processing, as is hereinafter explained, of the digital output, as required by the invention, to produce processed digital data on DSP bi-directional output busses 44.

Data formatter 46 is coupled between DSP 42 and digital-to-analog-converters "CDACs") 49. The DSP bidirectional output busses 44 of the DSP 42 are connected to data formatter 46. Data formatter 46 is connected to DACs 49 through two serial data lines 48. Two of the processed digital outputs 44 are multiplexed onto each of the serial data lines 48 by data formatter 46. The serial data lines 48 are coupled to DACs 49 which produce analog outputs 50, 52, 54, and 56. The analog outputs 50, 52, 54, and 56 can be used as test points or for other purposes. In the preferred embodiment, DACs 49 are multiplexing "dual DACs", C54328 manufactured by Crystal Semiconductor of Austin, Tex. The data formatter 46 also operates as a gateway between a SCSI (small computer systems interface) port 62 and DSP 42.

Data formatter 46 operates under the control of an I/O processor 70. The data formatter 46 is connected to the I/O processor 70 through an I/O bus 60. I/O processor 70 is further connected to a SCSI port 62 through SCSI control bus 68 and to capstan motor control 74 through capstan control bus 72. I/O processor 70 configures data formatter 46 in response to commands sent or received through SCSI port 62. The commands comply with the industry standard SCSI protocol, which governs transfers across SCSI data bus 64 connected between SCSI port 62 and PC controller 66. The commands specify the transfer attributes including: the type of transfer, i.e., read or write; the source and destination addresses; and the corresponding number of bytes. The I/O processor 70 configures data formatter 46, by writing to registers within data formatter 46, in order to accomplish the transfer specified by the command.

SCSI port 62 is coupled to PC controller 66 across SCSI bus 64. PC controller 66 is able to receive processed digital data from DSP 42 across SCSI bus 64 as well as send configuration information to DSP 42 across SCSI bus 64. The PC controller 66 can perform further processing, if necessary, on the processed digital data and display, print or store the resulting output. In addition to the ECG patient signals, the PC controller 66 also receives the characterization signal. The characterization signal received in the processed digital data is examined by the PC controller to determine the compensation required by DSP 42. The PC controller 66 transmits filter coefficients via SCSI bus 64 to DSP 42 in order to accomplish the required compensation, as is described in greater detail below. Digital signal processing can be allocated between DSP 42 and the PC controller 66.

Figure 2:
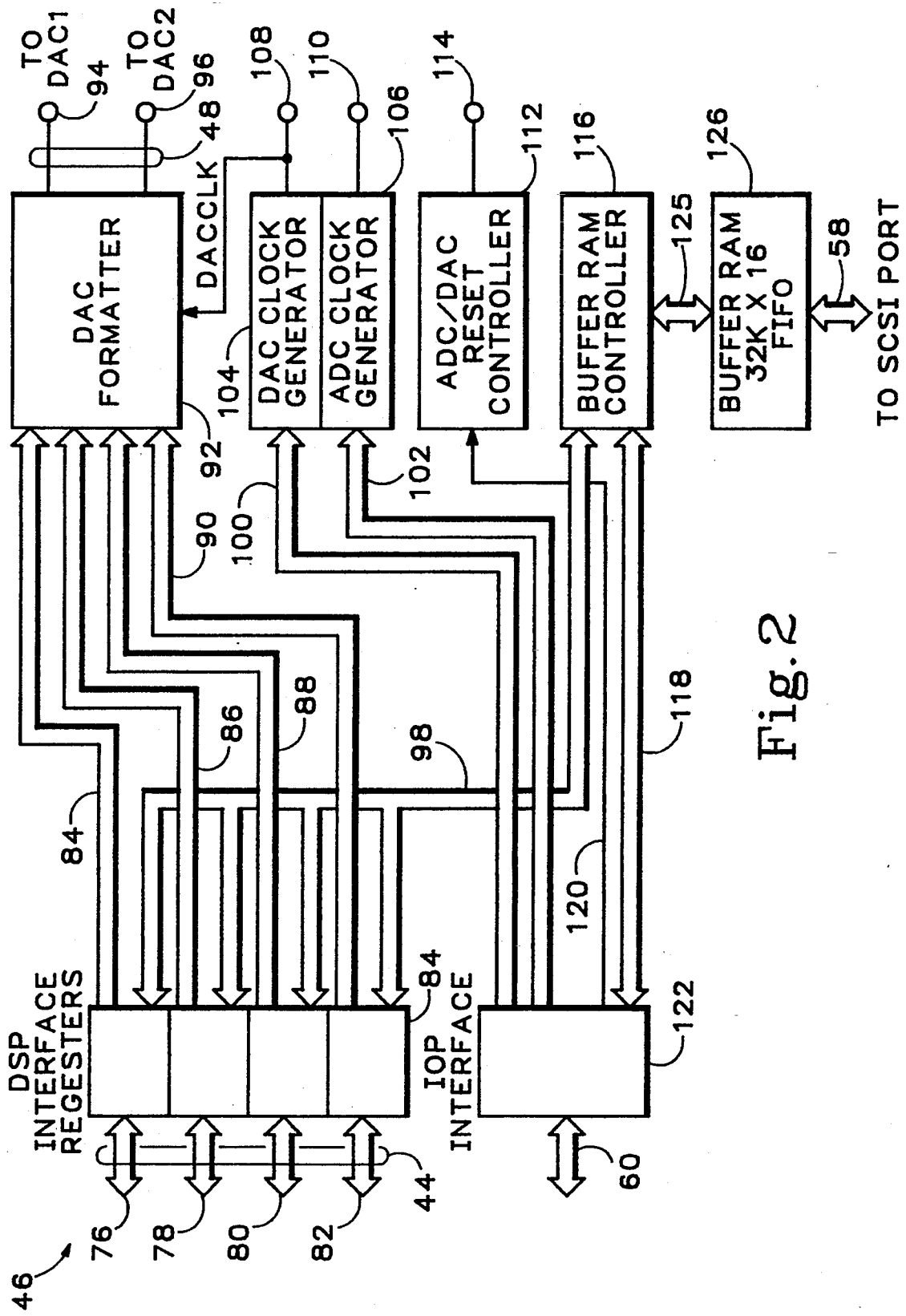
FIG. 2 is a block diagram of data formatter 46 shown in FIG. 1 implemented as an integrated circuit.

Referring now to FIG. 2, a block diagram of the data formatter 46 of FIG. 1 is shown. In the preferred embodiment, formatter 46 is implemented as an integrated circuit ("IC") gate array. Processed digital outputs 44, in FIG. 1, are comprised of four separate bidirectional busses 76, 78, 80, and 82, one for each digital signal processor. The bidirectional busses 76, 78, 80, and 82 connect to a corresponding set of DSP interface registers 84, one set connected to each bidirectional bus. In the preferred embodiment, each DSP 42, in FIG. 1, interfaces with a set of read/write registers used to transfer data to and from a buffer ram 126, the other three DSP's and a DAC formatter 92. Additionally, some registers are used for control functions.

Each register set is connected to DAC formatter 92 through a corresponding DAC interface bus 84, 86, 88, and 90. The DAC interface busses pass the processed digital data from the respective digital signal processor to the DAC formatter 92. The DAC formatter 92 interleaves and serializes the processed digital data received from two DAC interface busses onto a single serial data line, either 94 or 96, with the other two DAC interface busses being output in a similar manner on the remaining serial data line. The DAC formatter 92 receives a clock signal 108 from DAC clock generator 104, which clocks out serial data output on the serial data lines 94 and 96.

An I/O processor (IOP) interface 122 interfaces the data formatter to the I/O processor (not shown in FIG. 2) through IOP bus 60. The IOP interface 122 directs the data present on IOP bus 60 to the appropriate destination. The IOP interface 122 can direct the data on IOP bus 60 to DAC clock generator 104 over bus 100, or to ADC clock generator 106 over bus 102. In this way, I/O processor 70 (in FIG. 1) can write data to DAC clock generator 104 to establish the necessary clock frequency on DAC clock 108 and, similarly, can write data to ADC clock generator 106 to establish the necessary clock frequency on ADC clock 110. IOP interface 122 also interfaces to a buffer RAM controller 116 over bidirectional buffer RAM controller bus 118. IOP interface 122 can send or receive data from the buffer RAM controller 116 over bidirectional buffer RAM controller bus 118. IOP interface 122 also provides reset line 120 connected to ADC/DAC reset controller 112, which, in turn, produces reset output 114.

Buffer RAM controller 116 is connected to all four sets of buffer RAM registers in DSP interface registers 84 via bus 98. Buffer RAM controller 116 is also connected to buffer RAM 126 through RAM controller bus 125. Communication between the DSP interface registers 84 and buffer RAM 126 and between the IOP interface 122 and buffer RAM 126 is controlled by buffer RAM controller 116. The buffer RAM controller 116 is responsible for sequentially polling the DSP and IOP interface registers and transferring any data found thereby to RAM buffer 126. Also, the buffer RAM controller 116 receives data from the buffer RAM 126 and transfers the data to the appropriate DSP interface register. In addition, the buffer RAM controller coordinates transfers of data to and from IOP interface 122. Buffer RAM 126 is connected directly to SCSI port through RAM bus 58. In the preferred embodiment, buffer RAM 126 is a 32K×16 dual ported bidirectional first-in-first-out (FIFO) RAM, which can be included as part of the data formatter 46 IC or as a stand-alone IC such as µPD42532 manufactured by NEC of Mountain View, Calif.

Figure 3:
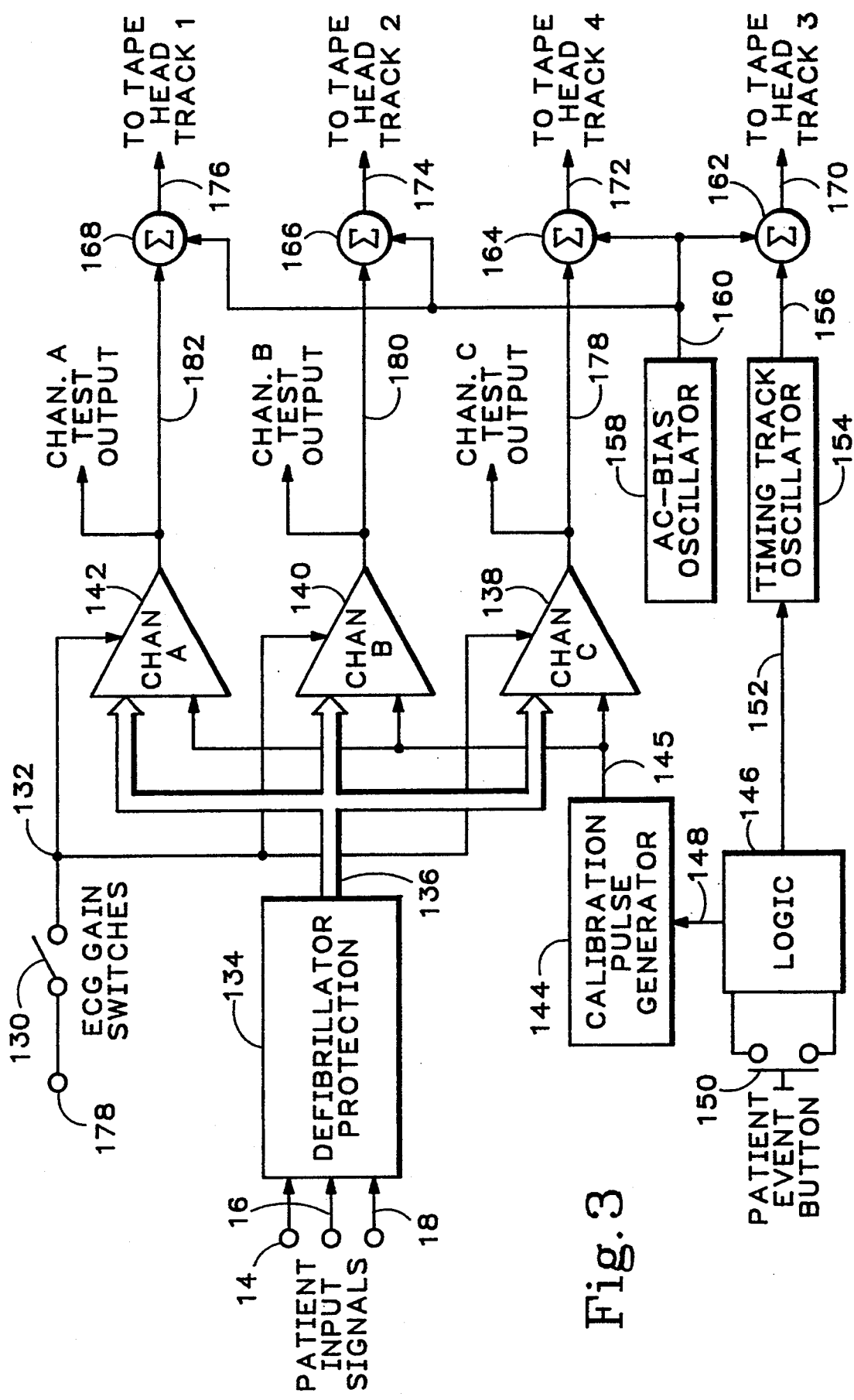
FIG. 3 is a detailed block diagram of the Holter recorder shown in FIG. 1.

Turning now to FIG. 3, recorder 12 of FIG. 1 is shown in greater detail. The patient signals 14, 16, and 18, which are each differential inputs, are received by a defibrillator protection network 134, which provides protection for both the recorder and the patient in the event of a patient being defibrillated while connected to the recorder. The outputs 136 consist of three differential signal pairs from network 134.

Each pre-emphasis amplifier 138, 140, and 142 receives a gain setting signal on line 132 from ECG gain switch 130. The gain switch 130 allows the gain of each amplifier to be individually set to one of two present values. Pre-emphasis amplifiers 138, 140, and 142 also receive calibration and characterization signals over output lines 145 frown a calibration pulse generator 144. The calibration pulse generator is connected to a logic circuit 146 through input lines 148. Control signals are transmitted on input lines 148 during a characterization/calibration period. Calibration pulse generator 144 transmits characterization and calibration signals on output lines 145 for approximately the first 8½ minutes after the recorder power is turned on.

Patient event button 150 is connected to logic circuit 146. Event button 150 is pressed by the patient during a physical event that the patient wishes to note. When event button 150 is pressed, logic circuit 146 amplitude-modulates timing track oscillator 154 with control signal 152. The amplitude modulation of oscillator 154 is used to indicate a patient event on the timing track.

Pre-emphasis amplifiers 138, 140, and 142 have single-ended outputs 178, 180, and 182, respectively, which are connected to summers 164, 166, and 168, respectively, as well as being supplied as output test channels. The single-ended outputs 178, 180, and 182 are combined with an AC-bias signal on bias line 160 produced by an AC-bias oscillator 158. The AC-bias signal is required in head output lines 172, 174, and 176 in order for the head output signals to be properly recorded by the tape head. Similarly, oscillator output 156 is combined with AC-bias signal 160 by summer 162 to produce head output line 170. Summers 162, 164, 166, and 168 are implemented with passive networks, described in detail below.

Figure 4:
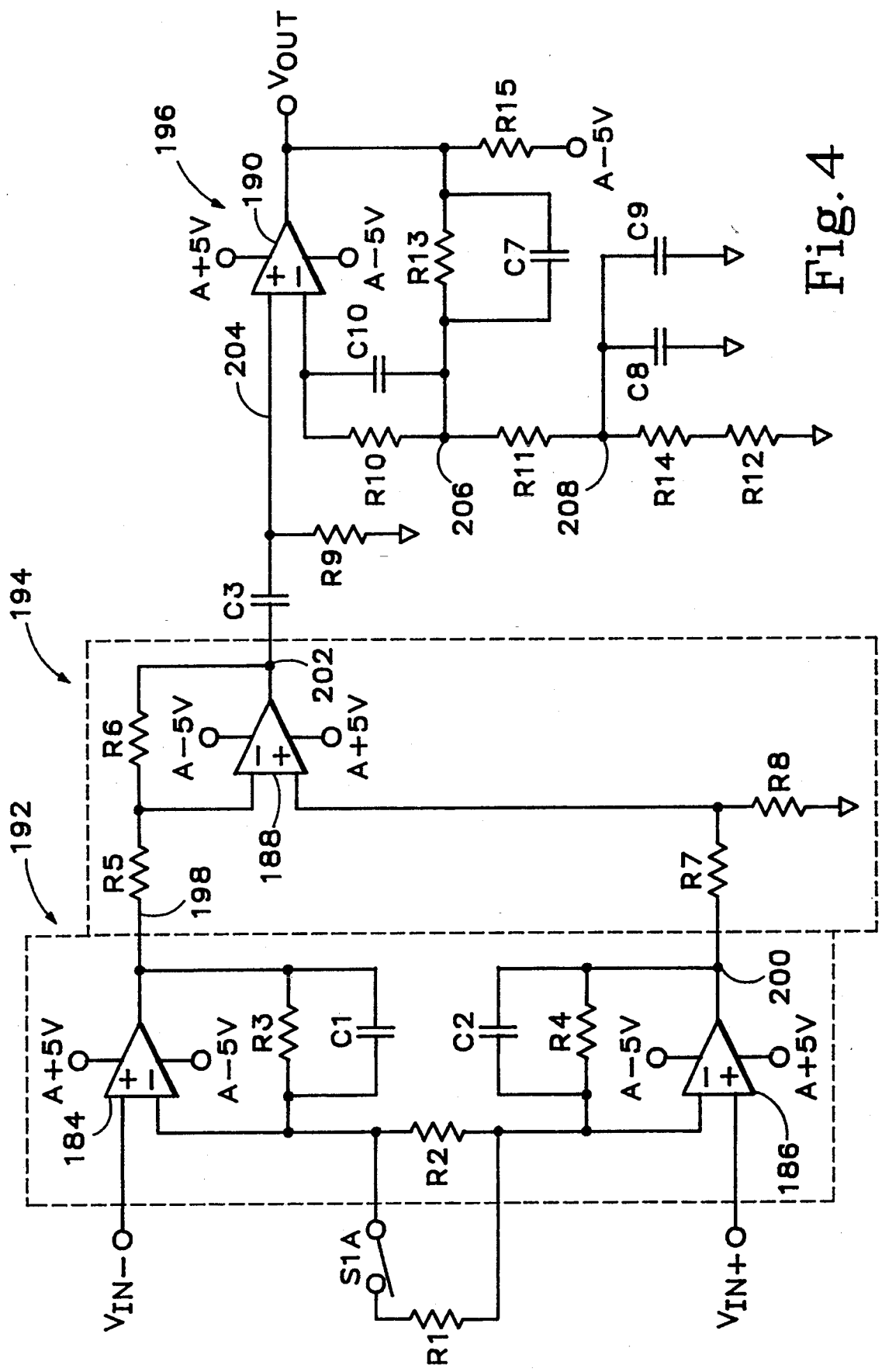
FIG. 4 is a detailed schematic of an individual pre-emphasis amplifier contained in the recorder of FIG. 1.

Referring to FIG. 4, a detailed schematic of an individual pre-emphasis amplifier, i.e., 138, 140, and 142 of FIG. 3, is shown. The pre-emphasis amplifier is comprised of three separate stages: a differential amplifier 192 having a predetermined high frequency rolloff, a differential input (VIN+ and VIN−) and a differential output (198 and 200); a differential-to-single-ended converter 194 having a differential input coupled to the output of the differential amplifier and an output 202; and an output amplifier 196 having a predetermined high frequency boost, an input coupled to the output of the differential-to-single-ended converter, and an output for providing a single-ended boosted voltage.

The differential amplifier stage 192 receives a differential input signal consisting of a positive input VIN+ and a negative input VIN−. The differential amplifier stage 192 has a first operational amplifier ("op-amp") 184 and a second operational amplifier 186 coupled to the negative input VIN− and the positive input VIN+, respectively. The negative input VIN− is connected to the positive input of the first op-amp 184. Coupled between the negative input and the output of the first op-amp 184 is a first feedback network, consisting of a parallel combination of resistor R3 and capacitor C1. Similarly, the positive input of the second op-amp 186 is connected to the positive input VIN+. Coupled between the negative input and the output of the second operational amplifier 186 is a second feedback network, consisting of the parallel combination of resistor R4 and capacitor C2. In the preferred embodiment, resistors R3 and R4 are about 4.64 KΩ and capacitors C1 and C2 are about 0.1 uF to produce a rolloff frequency of about 300 hertz. The output 198 of the first op-amp 184 and the output of the second op-amp 186 form the differential output of differential output stage 192.

Coupled between the negative inputs of the first and second op-amps 184 and 186 is a third network comprising a first resistor R2; a second resistor R1; and a switch S1A for coupling either the first resistor, or the parallel combination of the first and second resistors, to the negative inputs of the first and second op-amps. In the preferred embodiment, first resistor R2 is about 2.15 KΩ and second resistor R1 is about 1.78 KΩ. When switch S1A is open, the first resistor R2 is coupled between the negative inputs of first 184 and second 186 op-amps. When switch S1A is closed, however, the parallel combination of first resistor R2 and second resistor R1 is coupled between the negative inputs of first 184 and second 186 op-amps. Thus, the gain of the differential input stage 192 can be set to two distinct settings by opening or closing the switch S1A. In the preferred embodiment, using the values indicated above, the gain of the differential input stage is reduced by about one-half when switch S1A is open.

The differential output 198, 200 of differential input stage 192 is coupled to a differential-to-single-ended converter 194. The differential-to-single-ended converter 194 includes an op-amp 188 and four gain-setting resistors. The first differential output 198 is coupled to the negative input of op-amp 188 through a first resistor R5. A second resistor R6 is coupled between the negative input and the output of op-amp 188. The second differential output 200 is coupled to the positive input of op-amp 188 through a third resistor R7. A fourth resistor R8 is coupled between the positive input of op-amp 188 and ground. In the preferred embodiment, the first, second, third, and fourth resistors are about 10 KΩ, and the overall gain of converter 194 is unity.

The single-ended output 202 is AC-coupled to output amplifier 196 through high-pass resistor-capacitor network including resistor R9 and capacitor C3. Coupling capacitor C3 is coupled between single-ended output 202 and output amplifier 196 input 204. Resistor R9 is coupled between the input of output amplifier 196 and ground. In the preferred embodiment, coupling capacitor C3 is comprised of four parallel 1 μF capacitors, and resistor R9 is about 825 KΩ.

Output amplifier 196 is comprised of an operational amplifier 190 having a positive input forming the input to the output amplifier, a negative input, and an output forming the output of the output amplifier $V_{OUT}$. A capacitor C10 and a resistor R10 are coupled to the negative input of op-amp 190 and to a node 206. The parallel combination of resistor R13 and a capacitor C7 is coupled between the output of op-amp 190 and node 206. Coupled between node 206 and node 208 is resistor R11, and coupled between node 208 and ground is the parallel combination of resistor R12 and R14 in a first leg, capacitance C8 in a second leg, and capacitance C9 in a third leg.

The parallel combination of the three legs introduces a zero in the frequency response of the output of output amplifier 196. In the preferred embodiment, resistor R12 is about 9.09 KΩ, R14 is about 422Ω, capacitance C8 is about 0.68 μF, and capacitance C9 is about 0.047 μF producing a rolloff frequency of about 30 hertz. This results in a greater gain at the higher frequencies than the lower frequencies, referred to herein as pre-emphasis. A pole is introduced by the parallel combination of resistor R13 and capacitance C7, leveling out the frequency response at the corresponding rolloff frequency. In the preferred embodiment, resistor R13 is about equal to 196 KΩ and capacitance C7 is about 4700 pF, producing a rolloff frequency of about 170 Hz. The overall gain of the amplifier increases gradually above 10 hertz to a peak of about 10 dB of gain at about 150 hertz. If pre-emphasis is not desired, capacitors C8 and C9 can be removed from the circuit.

Figure 5A:
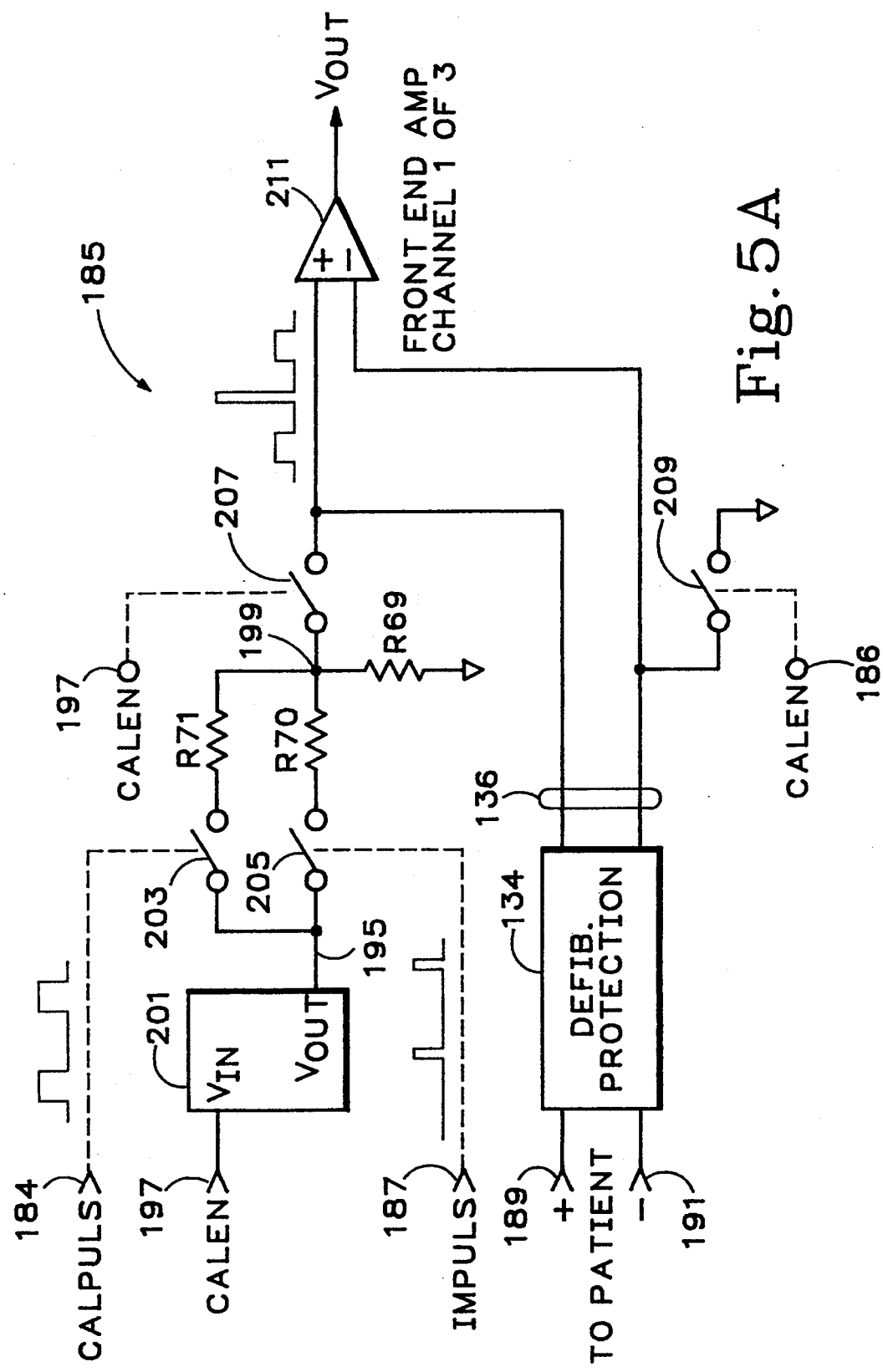
FIG. 5A is a block diagram of a calibration pulse generator contained in the recorder of FIG. 1.
Figure 5A:
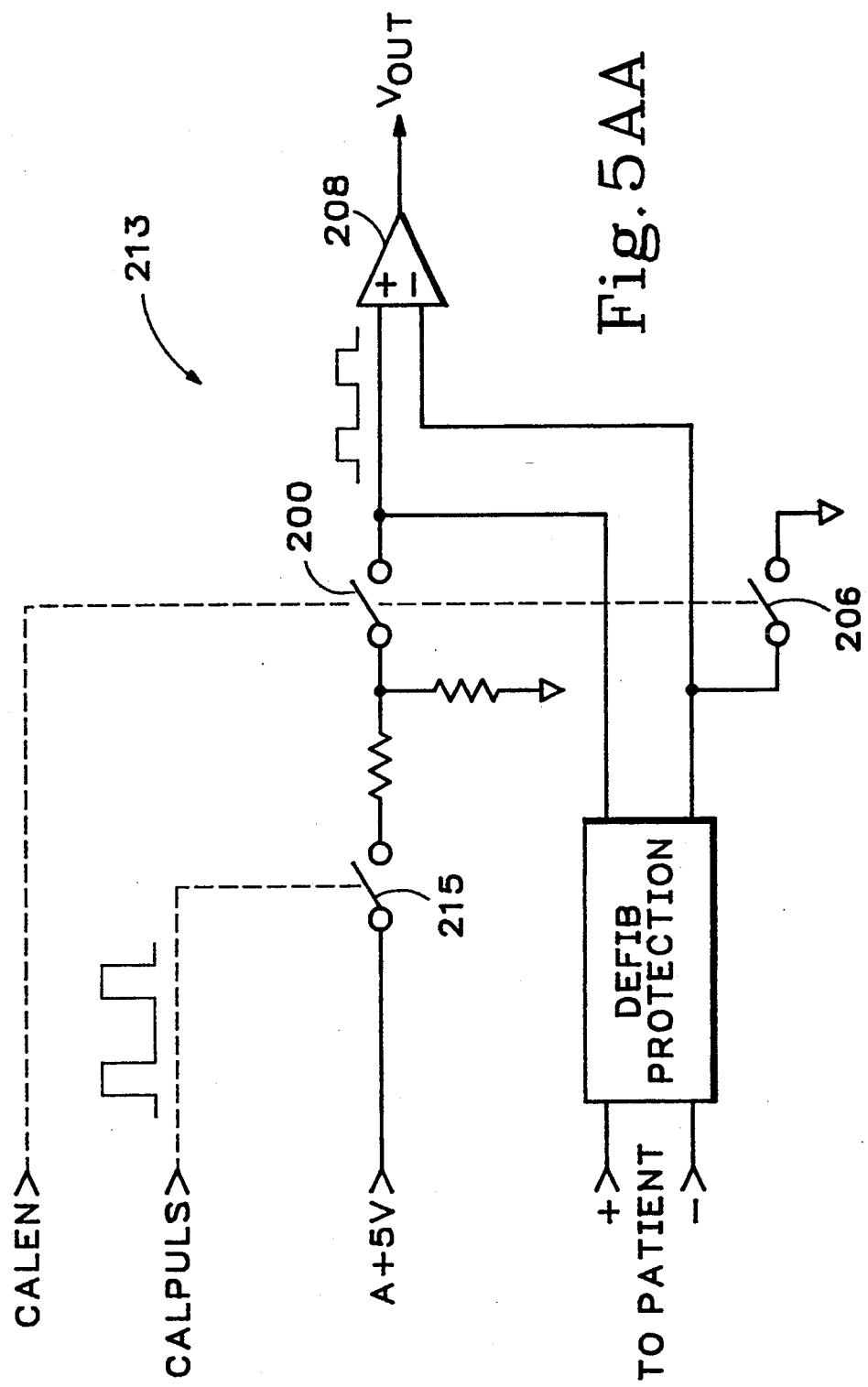

Referring to FIG. 5a, a block diagram of the calibration pulse generator (144 in FIG. 3) is shown generally at 185. A patient input differential signal at nodes 189 and 191 is coupled to defibrillator protection circuit 134. The output 136 of defibrillator protection circuit 134 is coupled to the input of pre-emphasis amplifier 211, representing any of pre-emphasis amplifiers 138, 140, and 142 shown in FIG. 3. A calibration enable line 197 (CALEN) is connected to a control input of reference voltage generator 201. In addition, calibration enable line 197 is connected to the control inputs of analog switches 207 and 209. When a calibration enable signal on calibration enable line 197 is asserted, with an appropriate logic level, e.g, 5 volts, the reference voltage generator 201 produces a reference voltage on reference output 195. The assertion of calibration enable signal also closed switches 207 and 209. Alternatively, when calibration enable signal is deasserted, e.g., zero volts, switches 207 and 209 are opened.

The reference output 195 is connected to the inputs of analog switches 203 and 205. The output of analog switch 203 is connected to resistor R71. Similarly, the output of analog switch 205 is connected to resistor R70. Resistors R70 and R71 are connected at a common node 199 with resistor R69, with resistor R69 being further coupled to ground. The control input of analog switch 203 is connected to calibration line 184, and the control input of analog switch 205 is connected to input line 187.

The calibration pulse generator produces the calibration and characterization pulses which are recorded onto the tape to provide the necessary information to the playback transport to accomplish the system calibration and characterization. The calibration pulse is produced by generating a calibration control signal on calibration line 184 when the calibration enable signal is asserted. The calibration control signal closes analog switch 203 causing the control voltage to be impressed across resistors R69 and R71. The exact amplitude of the calibration pulse produced on node 199 is determined by the voltage divider circuit of resistor R71 and resistor R69. The calibration signal itself can also serve as a characterization signal for determining the Holter recorder and playback unit response according to digital processing steps that are described below.

Alternatively, a characterization pulse can be a repetitive impulse signal that is interleaved with the pulses of the calibration pulse train. The impulse signal IMPULS closes analog switch 205 causing the output voltage to be impressed across resistor R70, and divided down by the voltage divider of resistor R70 and resistor R69. In both cases, the assertion of the calibration enable signal CALEN closes analog switch 207 causing the signal on node 199 to be coupled to the positive input of pre-emphasis amplifier 211. The assertion of the calibration enable signal also closes analog switch 209 shorting the negative input of pre-emphasis amplifier 211 to ground. In the preferred embodiment, the reference voltage is about 4.95-5.05 volts. Resistor R69 is about 69.5Ω, resistor R70 is about 182 KΩ, and resistor R71 is about 348 KΩ. The corresponding characterization signal has an amplitude of 2 mVolts, while the corresponding calibration signal has an amplitude of 1 mVolt, given that the two signals are mutually exclusive.

Logic block 146 (see FIG. 3) generates the calibration signals and impulse signals. In addition, the logic block is responsible for generating the clock signals required by timing track oscillator 154. The logic block 146 consists of a counter circuit clocked by a fixed frequency clock generator and some output logic. The calibration signal, in the preferred embodiment, is a repetitive rectangular pulse train. The calibration pulses are automatically disabled after 512 seconds. The calibration pulses can be manually disabled in a factory test system. To ensure data integrity, however, no provisions have been made for the user to disable or shorten the calibration interval. Preferably, the clock generator produces a 32 KHz clock signal which is divided down by the counter circuit to produce the 2048 Hz required by the AC-bias oscillator and the 32 Hz signal required by timing track oscillator 154. In the embodiment of FIG. 5A, the repetitive characterization impulse signals are interleaved between successive calibration pulses.

Another embodiment of the calibration pulse generator of FIG. 5A, which is preferred, is indicated generally at 213 in FIG. 5AA. In circuit 213, the calibration pulses are used for system characterization; therefore, separate characterization impulses are not generated. When CALEN is asserted in circuit 213, the inverting input of amplifier 208 is grounded through switch 206. The non-inverting input of amplifier 208 is connected to a voltage divider tap. The signal CALPULS turns an analog switch 215 on and off at the correct duty cycle for the desired calibration pulses. A +5 V is divided by the voltage divider to give a 1.00 mV pulse at the amplifier input.

Figure 5B:
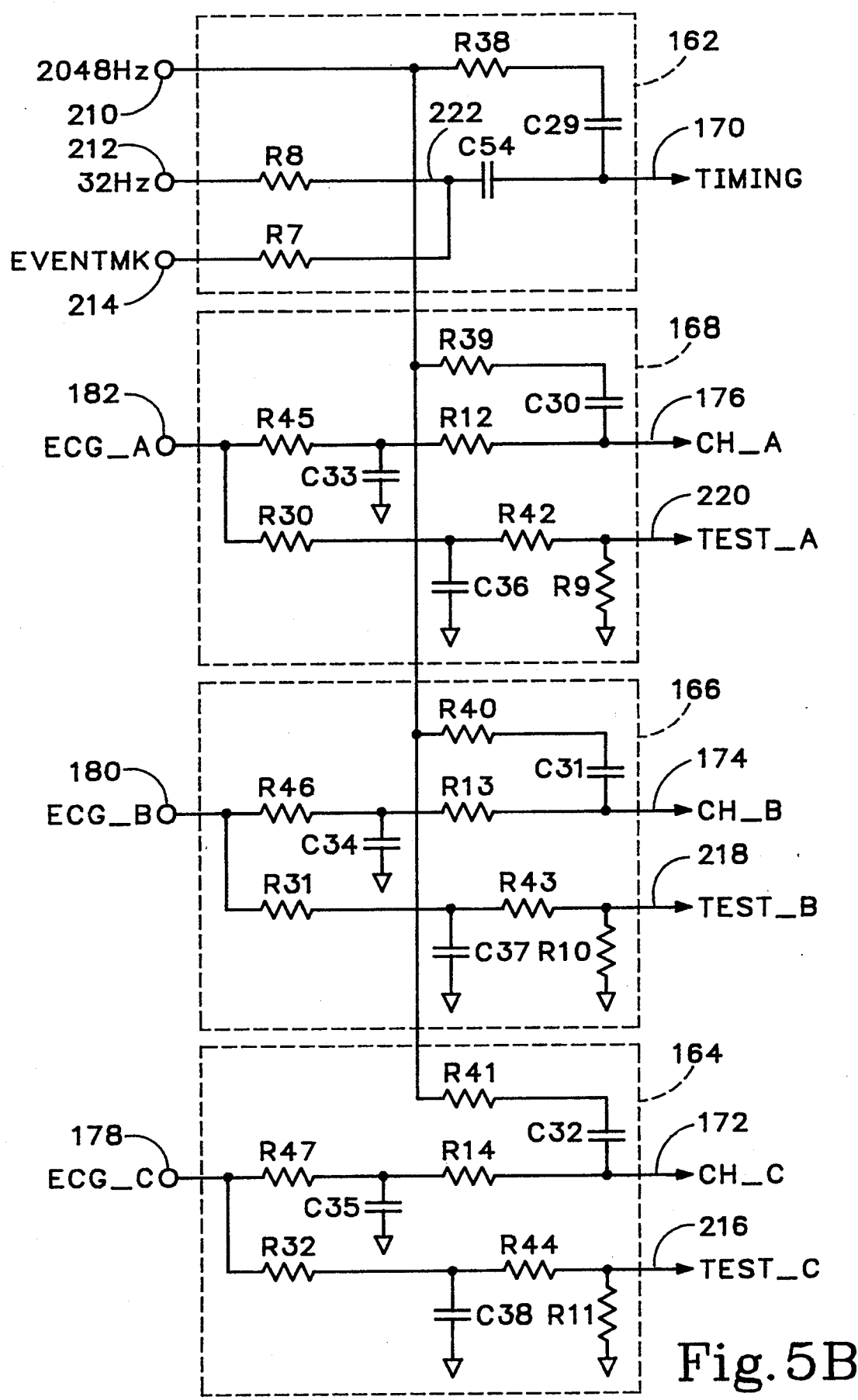
FIG. 5B is a schematic of a summing circuit contained in the recorder of FIG. 3.

Referring to FIG. 5B, a schematic of the combined summer circuits, i.e., 162, 164, 166, and 168 of FIG. 3, is shown. The primary function of the summer circuit is to sum the 2048 Hz AC-bias signal with the actual signals to be recorded on the cassette tape. An input line 210 carrying the 2048 Hz AC-bias signal is AC-coupled to each of head output lines 170, 172, 174, and 176 through a series combination resistor and capacitance. Input line 210 is connected to head output line 170 through the series combination of resistor R38 and capacitance C29. Input line 210 is connected to head output line 172 through the series combination of resistor R41 and capacitance C32. Input line 210 is connected to head output line 174 through the series combination of resistor R40 and capacitance C31. Input line 210 is connected to head output line 176 through the series combination of resistor R39 and capacitance C30. In the preferred embodiment, each resistor is about 7.50 KΩ and each capacitance is about 0.1 uF.

Input line 212, carrying the 32 Hz timing signal, and input line 214, carrying an event mark, are connected in parallel through resistor R8 and R7, respectively, to node 222. Node 222 is AC-coupled through capacitance C54 to head output line 170. Head output line 170 is dedicated to transmitting timing information to cassette tape. The timing information includes both the fixed 32 Hz timing signal and the random event marks. The fixed timing signal allows the playback unit to compensate for fluctuations in the speed of recording or playback which could adversely affect the calculations of heart beat. The event marks allow the playback unit to correlate the patient input signals to the actuation of the patient event button.

Single-ended output 178 is coupled to head output line 172 through the network comprised of R47, C35 and R14. Similarly, output 180 is coupled to head output line 174 through the network comprised of R46, C34, and R13; output 182 is coupled to head output line 176 through the network comprised of R45, C33 and R12. In the preferred embodiment, Resistors R12, R13, and R14 are about 6.81 KΩ, capacitors C33, C34, and C35 are about 0.1 μF, and resistors R45, R46, and R47 are about 100Ω.

Each of the single-ended outputs is also connected to an additional network to provide test outputs 216, 218, and 220, respectively. The test outputs can be used to monitor the recorder input signals and verify patient lead setup. Single-ended output 178 is connected to test output 216 through the network consisting of R32, C38, R44, and R11. Single-ended output 180 is connected to test output 218 through the network consisting of R31, C37, R43, and R10. Single-ended output 182 is connected to test output 220 through the network consisting of R30, C36, R42, and R9. The respective test jack output networks add a de-emphasis pole to the signal path that cancels the recording amplifier pre-emphasis zero. In the preferred embodiment, resistors R30, R31, R32, R42, R43, and R44 are about 13.3 KΩ. Capacitors C36, C37, and C38 are about 1 μF, and resistors R9, R10, and R11 are about 133Ω. If a particular recorder is configured without the pre-emphasis feature, capacitors C36, C37, and C38 can be removed from the test jack output networks to eliminate the de-emphasis pole.

Referring to FIG. 5C, defibrillator protection circuit 144 (see FIGS. 3 and 4) is shown. Defibrillator protection is used to protect the recorder circuitry from the high voltage that would be present on a patient during a defibrillator discharge. Additionally, defibrillator protection protects the patient by preventing the recorder from shunting excessive defibrillator energy away from the patient. The circuit shown in FIG. 5c is replicated for each pair of patient monitor lines. A positive input 222 from the patient is connected to a positive output 226 through a current limiting resistor R80. The positive output 226 is connected to the cathode of diode 234 and to the anode of diode 236. The anode of diode 234 is connected to a protected negative supply voltage −Vclamp. The cathode of diode 236 is connected to a protected positive supply voltage +Vclamp. The positive output 226 is, therefore, clamped to within one diode drop of +Vclamp and −Vclamp.

Negative input 224 is similarly clamped through diodes 230 and 232. Negative input 224 is connected to negative output 228 through a current limiting resistor R81. The negative output 228 is connected to the cathode of diode 230 and to the anode of diode 232. The anode of diode 230 is connected to a protected negative supply voltage −Vclamp. The cathode of diode 232 is connected to a protected positive supply voltage +Vclamp. The negative output 228 is, therefore, similarly clamped to within one diode drop of +Vclamp and −Vclamp. In the preferred embodiment, current limiting resistors R80–R81 are ¼W carbon composition resistors of about 75 KΩ.

Positive supply voltage +Vclamp is generated from positive supply A+5 V. The A+5 V is coupled to voltage +Vclamp through a current limiting series resistor R83. +Vclamp is connected to the anode of diode 242. The cathode of diode 242 is connected to the anode of diode 244, whose cathode is connected to an analog ground. This circuit configuration ensures that voltage +Vclamp is within two diode voltage drops of analog ground.

Negative supply voltage −Vclamp is generated from negative supply A−5 V. A−5 V is coupled to voltage −Vclamp through a current limiting series resistor R82. −Vclamp is connected to the cathode of diode 238. The anode of diode 238 is connected to the cathode of diode 240, whose anode is connected to the analog ground. In this way, as for voltage +Vclamp, voltage −Vclamp is within two diode voltage drops of analog ground. In the preferred embodiment, current limiting series resistors R82–R83 are about 162 KΩ.

1. Cardiac Pacer Pulse Analysis Using Raw Uncorrected Data

The digitized data obtained from the analog to digital converter on lines 40 (in FIG. 1) is differentiated and considered unprocessed or "raw" data. Traditional ECG patent data is "processed" before being analyzed. This is data that has been compensated to remove distortion introduced by the record and playback processes. This compensation is typically achieved by conventional analog filtering methods. Previous conventional designs do not provide access to the unprocessed raw data. However, important information is more prevalent in the unprocessed raw data.

U.S. Pat. No. 4,291,703 and U.S. Pat. No. 4,532,934, which are both incorporated herein by reference, describe means for detecting cardiac pacer spikes in an analog Holter recorder and storing markers on the tape to represent these spikes. This is usually performed on a recording channel separate from the ECG signal. By using a recorder that boosts the frequency response with a pre-emphasis amplifier, like amplifiers 138, 140, 142, in FIG. 3, and analyzing this tape of raw boosted data, the spikes are more effectively detected in software.

Figure 6A:
FIGS. 6A–6C are illustrations of raw ECG signals with PACER information.
Figure 6B:
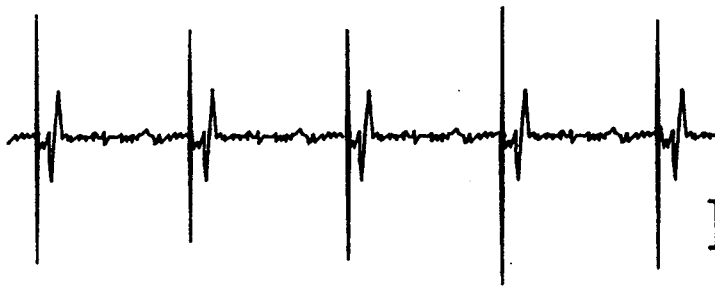
Figure 6C:
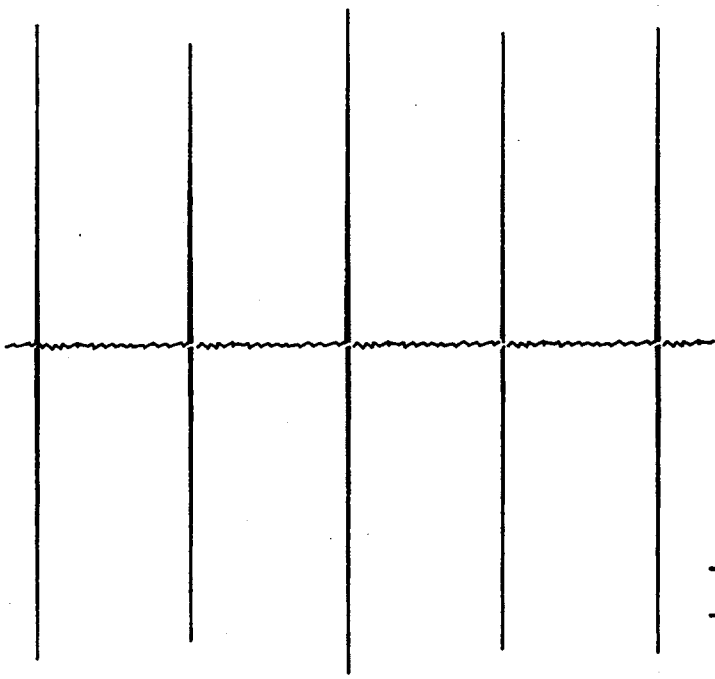

FIGS. 6A and 6B are illustrations of raw ECG signals taken from a patient with an implanted cardiac pacer and showing pacer-generated spikes appearing in the ECG signal. FIG. 6C, 7C is an illustration of a cardiac pacer truth tracing indicating where each spike occurs. The signals in FIGS. 6A–6B have been boosted using the pre-emphasis scheme illustrated in FIG. 4 and were obtained using a 12 lead cardiograph. Note that the data in FIGS. 6A–6B has not been processed to remove any signal distortion.

Figure 7A:
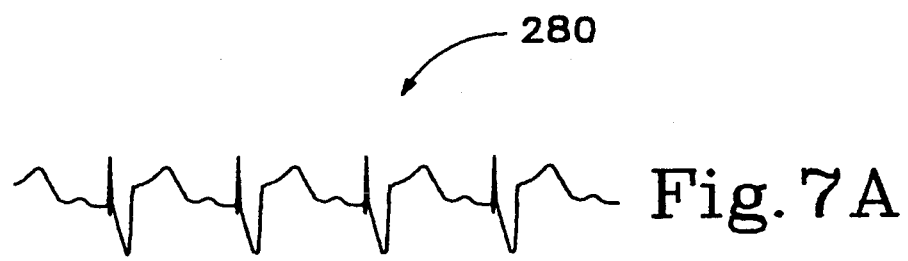
FIGS. 7A–7C are illustrations of processed ECG signals with PACER information.
Figure 7B:
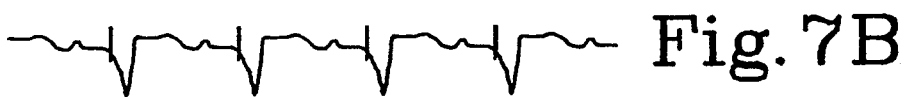
Figure 7C:

FIGS. 7A–7B illustrate the signals 6A–6B, respectively, after they have been processed. It can be seen that the pacer spike information is much more evident in the raw data in FIGS. 6A–6B than in the processed data of FIGS. 7A–7B. Therefore, the raw ECG patient data is utilized to process information not as readily detected in the post processed data. Processing of the raw data is performed by system 10 in FIG. 1 without using compensating filters in DSPs 42.

2. Signal Response of an ECG Recorder and Playback System

Consideration will be given now to the manner in which system 10, FIG. 1, falters played-back ECG signals in a manner which produces a substantially flat frequency response and a substantially linear phase response for system 10, FIG. 1. Several factors control the signal response of an ECG recorder and playback unit. Differentiation of recorded signals during playback causes low frequency roll off and a 90 degree phase shift. The physical characteristics of the playback head and a slow ECG recording speed cause high frequency roll off. These high and low frequency effects differ depending on the specific type of equipment used to record and play back the ECG data.

Figure 8:
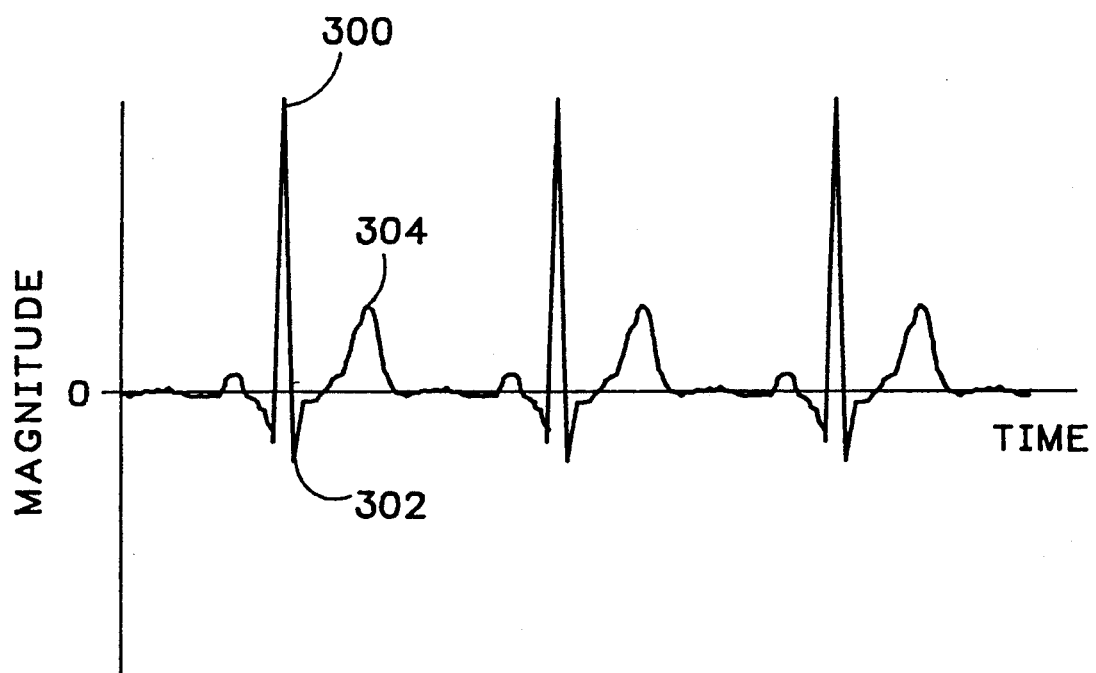
FIG. 8 is an illustration of an ECG signal prior to being fed into a recorder.
Figure 9:
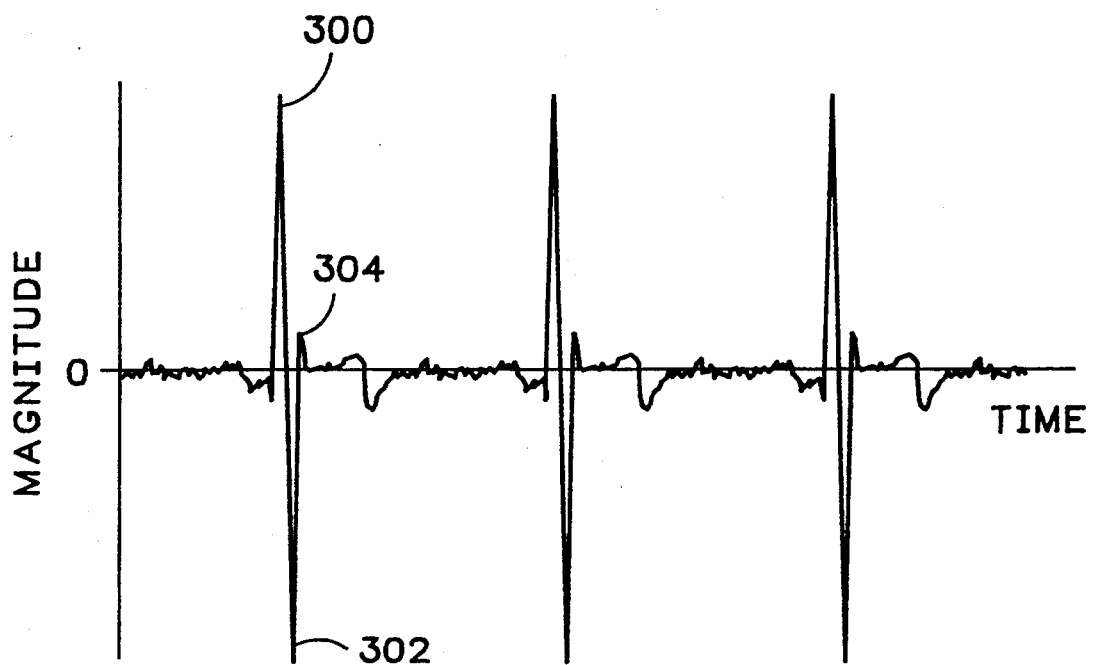
FIG. 9 is an illustration of the raw ECG signal of FIG. 8 after being recorded and played back at 120 times the real-time recording speed.

FIG. 8 is an illustration of patient ECG data prior to being fed into system 10. FIG. 9 is an illustration of the ECG data from FIG. 8 after being recorded and played back at 120 times the real-time recording speed in a prior art system. Ideally, the raw patient ECG data (FIG. 8) and the played-back patient ECG data (FIG. 9) should be the same. It can be seen that the amplitude and phase of the ECG signal in FIG. 9 is distorted at both positive and negative transitions with respect to the ECG signal of FIG. 8. For example, the large negative pulse 302 occurring immediately after the largest positive pulse 300 is larger in the played-back patient ECG data in FIG. 9. In addition, the smaller positive transition 304 immediately following the large negative transition 302, is attenuated in the ECG data shown in FIG. 9.

Figure 10:
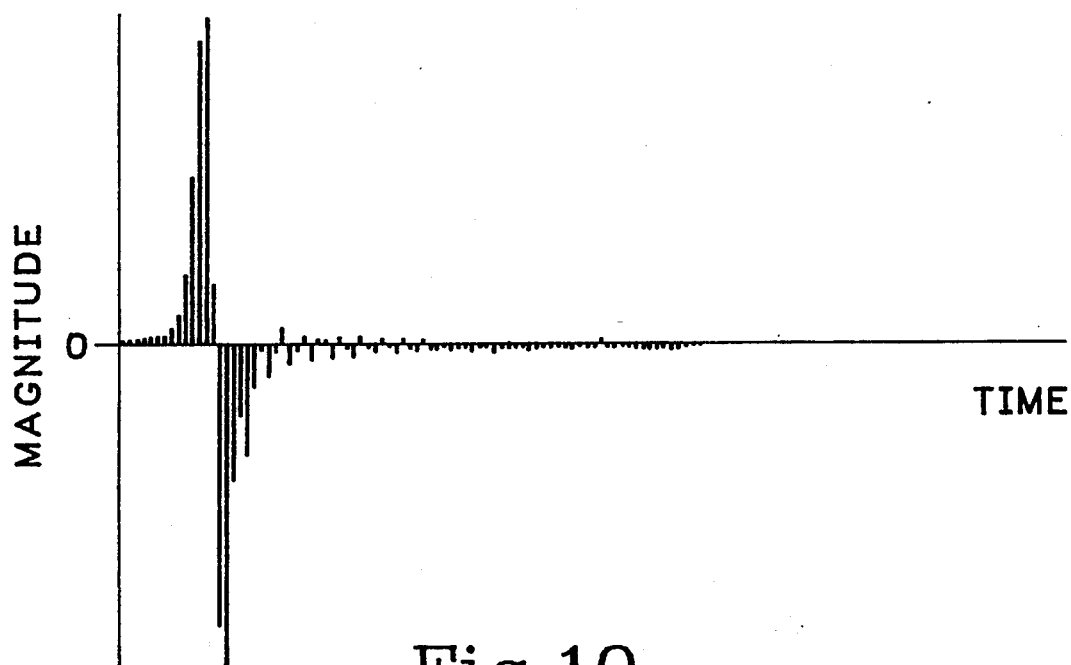
FIG. 10 is an illustration of an impulse signal after being recorded and played-back by a recorder and playback unit in accordance the invention.

FIG. 10 is an illustration of an impulse signal after being recorded, played-back at 120 times the real-time recording speed and digitized at a 55 kHz sampling rate by the prior art recorder and playback unit used to generate the ECG signal in FIG. 9. Each vertical line in FIG. 10 represents the magnitude of a digital sample.

Present proposed minimum standards (Association for the Advancement of Medical Instrumentation, Ambulatory Electrocardiograph Draft Standard, October, 1992) for ECG recorder/playback units specify an amplitude response within the frequency range of 0.67 Hz to 40 Hz between +0.83 dB to −3.0 dB. Phase response within this frequency range must be linear within 4 degrees at 1 Hz. For more accurate patient ECG data, it is desirable to increase the high frequency range beyond 40 Hz.

Figure 11:
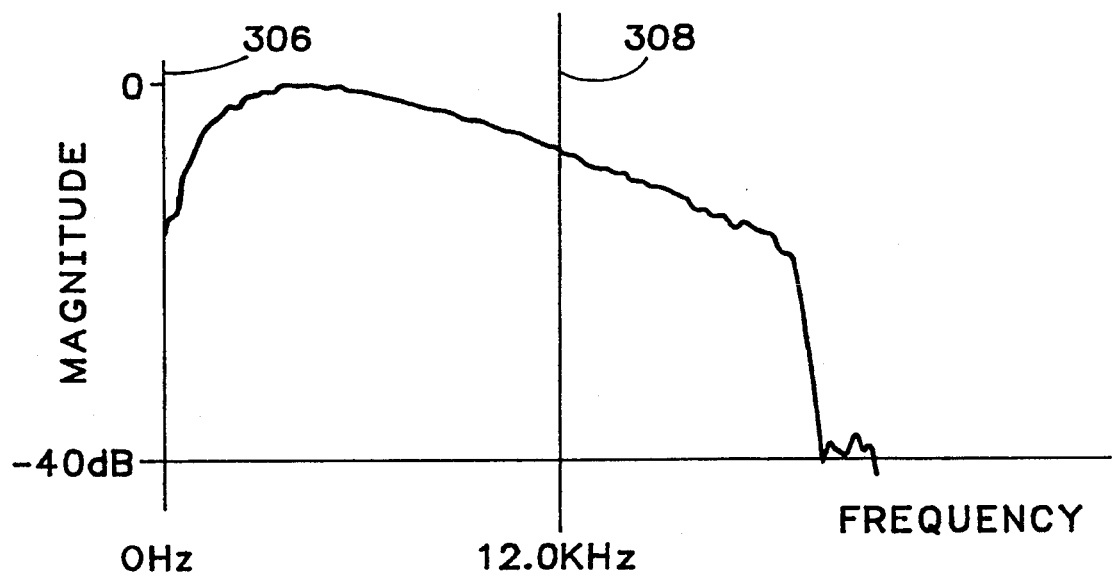
FIGS. 11, 12, and 13 illustrate the magnitude response, phase response, and group delay, respectively, of the recorder and playback unit.
Figure 12:
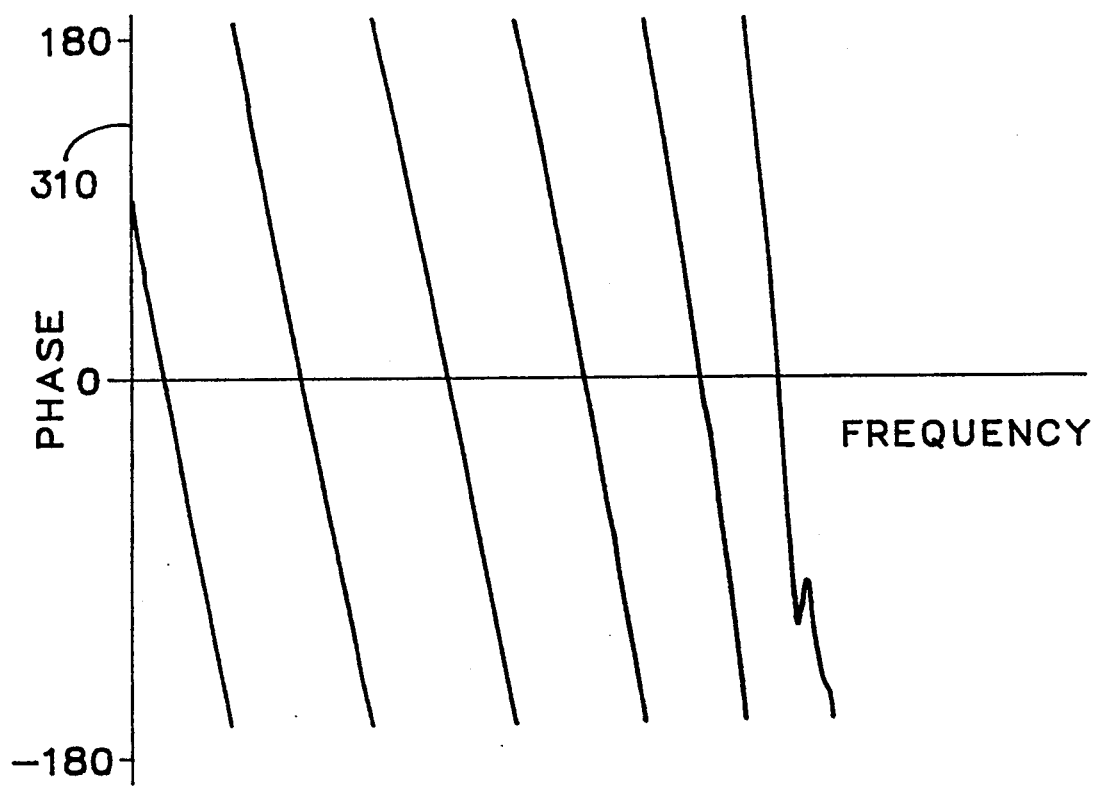
Figure 13:
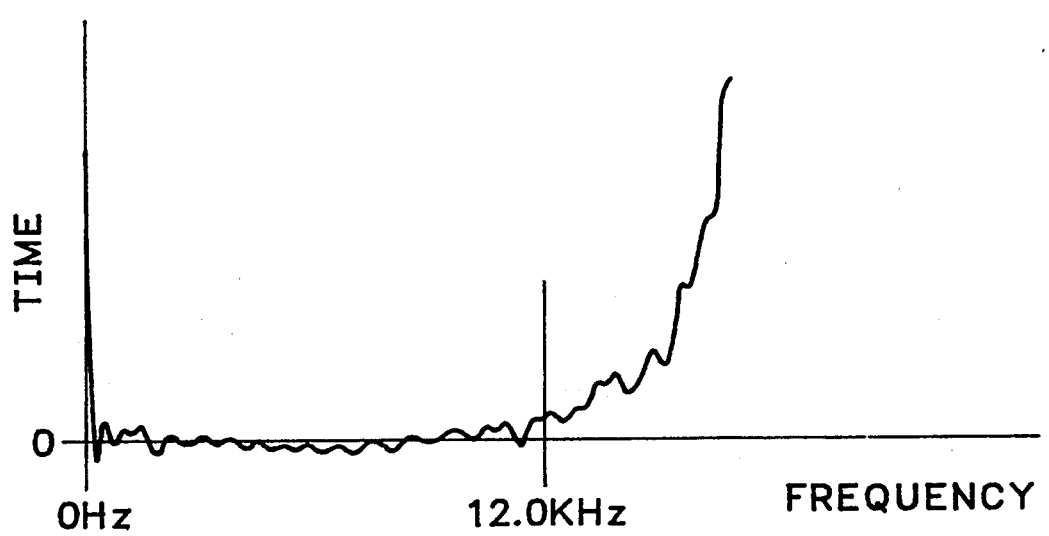

FIGS. 11, 12, and 13 illustrate the magnitude response, phase response, and group delay (all of which are referred to collectively herein as frequency response), respectively, of a typical Holter recorder and playback unit. The responses plotted in FIGS. 11, 12, and 13 are derived by sampling the impulse response (FIG. 10) at 55 kHz then performing a 4096 point fast Fourier transform (FFT). Referring to FIG. 11, vertical lines 306 and 308 define the lower and upper frequency boundaries respectively for a desired recorder and playback bandwidth from 0 to 12 kHz. The scale of the x-axis in FIG. 11 reflects the frequency of the signals coming off the playback head at 120 times the recording speed. For example, the frequency range of 0 to 12 kHz translates into a real time recording frequency range of 0 to 100 Hz (12.0 kHz/120).

If the recorder and playback unit operated ideally and had no filtering effect on the impulse signal, the magnitude response between vertical lines 306 and 308 would be flat. However, as illustrated in FIG. 11, the magnitude response of the system drops significantly at the low frequencies around horizontal line 306. The magnitude response also drops significantly at high frequencies occurring immediately prior to vertical line 308. The magnitude response drop-off of the recorder and the phase distortion of the playback unit at low and high frequencies cause the distortion in the played-back patient ECG data as illustrated in FIG. 9.

FIG. 12 is an illustration of the recorder and playback unit phase response. The phase of the impulse response for an ideal system should be linear within the desired frequency band with a phase at DC that is an integer multiple of 180 degrees. As can be seen, the phase response at DC (e.g. point 310) is offset approximately 90 degrees. Phase offset creates significant phase distortion even if the phase response of the system has a constant slope.

FIG. 13 is an illustration of the group delay for the phase response. Group delay is defined as the negative of the first derivative of the phase with respect to frequency, as follows:

$$\text{group delay} = -d\Theta(\omega)/d\omega,$$

where $\Theta$ = phase and $\omega$ = frequency.

The group delay helps to illustrate the nonlinear phase characteristics of the recorder and playback unit. For example, for a linear phase response, the group delay is constant within the desired frequency band, i.e., the waveform in FIG. 13 will be flat. However, the group delay in FIG. 13 increases at the low and high frequency limits of the desired frequency band (0 to 12.0 kHz). These increases indicate phase nonlinearities in the system.

The major source of non-linear phase response is the differentiation of flux in the playback head. An additional source of the nonlinear phase response is the three-dimensional placement of the magnetic dipoles in the recording medium. Since not all of the magnetic field on the tape has a purely longitudinal (along the path of the tape) direction, the playback head phase-shifts the recorded data. Nonlinear phase response also contributes to the signal distortion illustrated in FIG. 9.

Therefore, to reduce distortion in patient ECG data the recorder and playback phase response must be linear and extrapolate to an integer multiple of 180 degrees at DC.

To flatten the magnitude response and linearize the phase response of the system, a correction filter is applied to played-back patient ECG data. The correction filter compensates the medium and high ends of the frequency band magnitude response (i.e. the correction filter flattens the recorder and playback magnitude response within the desired frequency band) and corrects the nonlinear characteristics of the phase response. Thus, the correction filter increases the effective bandwidth of the record and playback unit.

The magnitude and phase response illustrated in FIGS. 11, 12, and 13 are not the same for each Holter recorder or playback unit. Therefore, a single precalculated correction filter cannot effectively compensate for the nonideal magnitude and phase characteristics of multiple systems. Since the magnitude and phase response for any one system change, even a correction filter customized for one particular system becomes mismatched with time. Prior art systems typically use an analog filter as the correction filter.

The solution is to characterize the recorder and playback frequency response each time patient ECG data is recorded and to generate a new correction filter from this most recent characterization data. This provides a customized correction filter that accurately compensates the magnitude and phase response for the specific system being used. In addition, the correction filter accounts for variations in any one system that can occur over time. As explained hereinafter, either an impulse or a step signal can be recorded and thereafter played back to characterize the system frequency response. When an impulse response is used, the processing to obtain the system frequency response after playback includes an integration step to compensate for the differentiation effect produced by the playback head. When a step pulse is used, an impulse is produced after playback because an impulse results from differentiation of a step pulse. When a step pulse is used, no integration is required to obtain an impulse response. The following mathematical analysis applies when either a step or impulse is used to characterize a system.

3. Mathematical Foundation for System Characterization Using an Impulse Response The overall process for characterizing a recorder and playback signal response and generating a customized correction filter is illustrated in FIGS. 14 and 15. The method for applying the correction filter to played-back patient ECG data is illustrated in FIG. 16. The terms used to describe FIGS. 14–16 are defined as follows:

$x(t)$ = patient ECG data $h(t)$ = recorder/playback unit signal response $h(n)$ = sampled $h(t)$ $y(t)$ = patient ECG data played-back from the recorder and playback unit $y(n)$ = sampled output from the recorder and playback unit $\{\ \}$ = discrete Fourier transform operation $^{-1}\{\ \}$ = inverse discrete Fourier transform operation $\delta(t)$ = impulse signal $H(k)$ = discrete frequency response of $h(n)$, a complex function with magnitude ($\|H\|$) and phase ($\angle H$)

FIG. 14 is a block diagram of a recorder and playback unit 312. Patient ECG data x(t) similar to that illustrated in FIG. 8 is recorded by system 312. The recorded patient ECG data is played-back generating played-back patient ECG data y(t) similar to that illustrated in FIG. 9. Ideally, the signal response h(t) should not significantly affect the magnitude or phase of x(t) within a desired frequency band. Thus, the output y(t) should be approximately equal to the input x(t). However, due to the non-ideal magnitude and phase response characteristics illustrated above in FIGS. 11–13, the output y(t) is distorted in comparison with the input x(t).

FIG. 15 is a block diagram illustrating a process for characterizing the frequency response of the recorder and playback unit and generating a correction filter response. The system is characterized by feeding an impulse signal δ(t) or a step response u(t) into the recorder and playback block 312. The output of block 312 is digitized by a sampler 313 to produce h(n). Using an impulse signal, the output from sampler 313 is the convolution of δ(n) and h(n), and is referred to as the system impulse response signal. The frequency response H(k) of the recorder and playback unit is derived from the impulse response signal by a system characterization block 314. Correction filter coefficients b(i) are then generated from H(k) by a correction filter generation block 316.

Since convolution in the time domain is equivalent to multiplication in the frequency domain, the discrete Fourier transform of the system impulse response can be described as follows:

$$\mathcal{F}\{\delta(n) * h(n)\} = \mathcal{F}\{\delta(n)\} \times \mathcal{F}\{h(n)\}.$$

The discrete Fourier transform of an impulse signal is equal to one, i.e.:

$$\mathcal{F}\{\delta(n)\} = 1.$$

The recorder and playback frequency response is therefore derived as follows:

$$\mathcal{F}\{\delta(n) * h(n)\} = \mathcal{F}\{\delta(n)\} \times \mathcal{F}\{h(n)\} = H(k).$$

Thus, system characterization block 3 14 determines the actual frequency response H(k) or, "characterizes" the recorder and playback unit. The correction filter magnitude response $\|B(k)\|$ is generated by applying the recorder and playback magnitude response $\|H(k)\|$ to a predetermined desired magnitude response. As explained above, it is desirable that the magnitude response of the system is flat within a given frequency band. Therefore, the desired magnitude response will be the same value for each frequency within the frequency band. $\|B(k)\|$ is then generated by dividing $\|H(k)\|$ by the desired magnitude response. For example, to generate a flat 0 dB magnitude response, the relationship between $\|H(k)\|$ and $\|B(k)\|$ is as follows:

$$\|H(k)\| \times \|B(k)\| = 1.$$

Thus, $\|B(k)\|$ is simply the inverse of $\|H(k)\|$. The correction filter phase response $\angle B(k)$ is generated by summing the recorder/playback phase response $\angle H(k)$ with a desired phase response. The phase relationship is defined as follows:

$$\angle B(k) + \angle H(k) = M \times k,$$

where M is a constant and k is the desired linear phase response. The magnitude and phase response for the correction filter are then transformed into the time domain. This generates the discrete time coefficients for the correction filter as follows:

$$\mathcal{F}^{-1}\{B(k)\} = b(i).$$

FIG. 16 is a block diagram that illustrates a process for applying the correction filter coefficients to played-back patient ECG data. Correction filter application block 318 uses a finite impulse response (FIR) filter to apply the correction filter coefficients generated in block 316 (FIG. 15) to the played-back patient ECG data y(n) from an integrator 317. Integrator 317 corrects the previously described effects of signal differentiation which is inherent in the playback process. The output of correction filter block 318 is ECG data that has been compensated to remove signal distortion caused by the limited bandwidth of the recorder and playback unit.

4. Overview of System Characterization Using an Impulse Response

FIG. 17 is a more detailed block diagram of system characterization block 314 of FIG. 15. An impulse train is recorded and played back in recorder and playback unit block 312.

If noise exists in the impulse response signal, an inaccurate correction filter could be generated. Therefore, using the repetitive nature of the impulse train, block 320 averages multiple impulse responses to remove random noise. The function of block 320 is illustrated in more detail in FIG. 19 and is described under the following part 6.

An analog tape playback head senses only the rate of change of tape flux. This differentiates the characterization impulse signal during playback. The averaged impulse response from block 320 is therefore integrated, as are subsequently played-back ECG signals, in block 322 (described in the following part 7) to remove the effects of playback differentiation.

As described above, the discrete Fourier transform of the recorder and playback impulse response signal is used to generate the frequency response. Therefore, a fast Fourier transform (FFT) is performed on the integrated impulse response in block 324. FFT block 324 outputs complex coefficients which comprise the phase and magnitude response of the recorder and playback unit.

5. Calibrating the Recorder and Playback Unit

In prior art systems, the technique for calibrating played-back patient ECG data involves recording a series of rectangular calibration pulses of known amplitude. The calibration pulses are then played back through the playback unit and passed through compensation filters to restore the pulse's original phase and frequency content. To calibrate the recorder and playback unit, the amplitude of the observed calibration pulses are measured and a single data scale factor is calculated accordingly. There are two problems with this technique. One is caused by variations from channel to channel, although some prior art systems provide for manual calibration of each channel. The second problem results from a phenomenon called tape dropout. Tape dropout is an apparent reduced recording level on a tape caused by variations in the recording medium. Both problems reduce calibration accuracy.

To improve playback calibration and eliminate the effects of tape dropout, a trimmed mean average is performed on a large number of samples. The samples are measured at the centers of observed calibration pulses. One implementation of this technique measures the amplitude of 100 calibration pulses on a single channel and stores the results in an array. The elements of the array are then sorted by value. The average of the mean 70% of the sorted list of amplitudes is calculated. By throwing out the extreme upper and lower 15%, the calibration becomes extremely insensitive to tape dropout. Also, the averaging reduces random noise. To correct the problem caused by variations from one channel to the next, a separate scale factor is used for each channel. The scale factors map the observed data from each channel to a value which more correctly represents the original data.

6. Impulse Response Averaging

FIGS. 18A and 18B illustrate impulse response signals 326 interleaved with calibration pulse signals 328. FIG. 18A illustrates the interleaved signals after being differentiated by the playback head in the playback unit. FIG. 18B illustrates the differentiated signal of FIG. 18A after it is integrated in block 322 of FIG. 17. The interleaved signal of FIG. 18B is therefore a close approximation of the interleaved calibration and impulse signals as recorded by the ECG recorder.

Each impulse response signal 326 is generated by recording and playing back an impulse signal with the system illustrated in FIG. 15. The existence and characteristics of the calibration pulses depend on the system used to record the ECG data. If present, calibration pulses 328 are typically generated at the beginning of an ECG recording tape.

The impulse signal can be interleaved with the calibration pulses at the beginning or end of the recording tape so that both system calibration and system characterization can be performed at the same time. This reduces time and also reduces the amount of magnetic tape required to calibrate and characterize the recorder and playback unit. Alternatively, the impulse signal can be generated before or after the calibration pulses, or separately in a system which does not use calibration pulses.

Due to the playback differentiation described above, impulse response signals 326 in FIG. 18A have a sharp positive transition followed immediately by a sharp negative transition. Typically, the positive and negative transitions of the impulse signal occur within a defined time. Therefore, an impulse can be identified by the number of data samples that exist between the positive and negative signal transitions. If present, calibration pulses exhibit generally the same signal characteristics but with a larger spacing between the positive and negative signal transitions.

To generate an averaged impulse response, each impulse must first be shifted to the same reference point. The precision of this shifting determines the effectiveness of the averaging process in removing random noise. For example, if the impulses are not accurately aligned, the wrong frequency components of each impulse will be added together, creating an inaccurate representation of the impulse response. However, precise impulse alignment normally is limited by the sample rate. The impulse averaging technique performed in block 320 (FIG. 17) provides a pulse alignment process which is more accurate than what is typically obtainable at a given sample rate.

Figure 19:
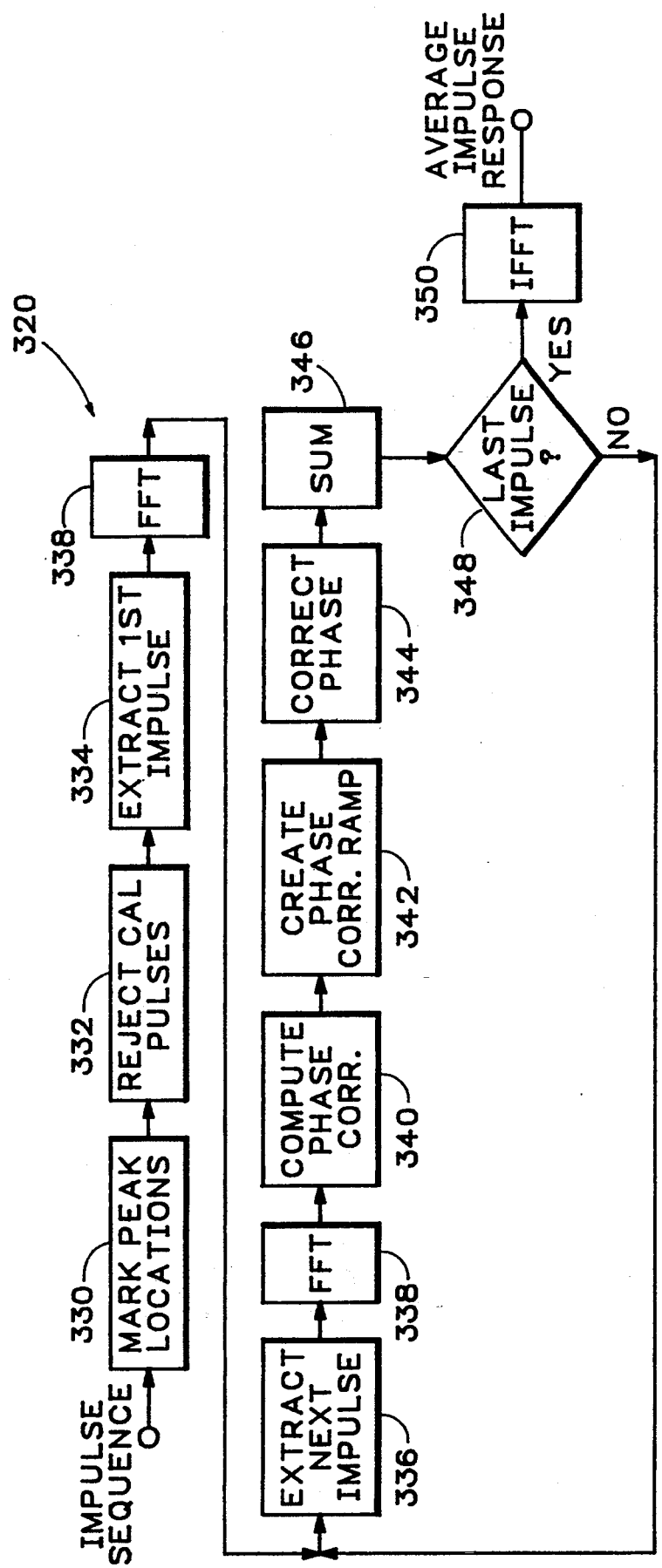
FIG. 19 is a detailed block diagram of averaging block 320 of FIG. 17.

The details of the averaging process in block 320 are illustrated in FIG. 19 wherein peak locations of the impulse response signal and calibration response signal are marked in block 330. The calibration pulses are then removed in block 332 and a first impulse is extracted from the impulse response signal in block 334. A second impulse is extracted in block 336 and the extracted impulses are transformed into the frequency domain in block 338. A phase correction value is determined from the impulse frequency response in block 340 and a phase correction ramp is created from this phase correction value in block 342. This phase ramp has a magnitude of 1 at all frequencies.

Figure 20:
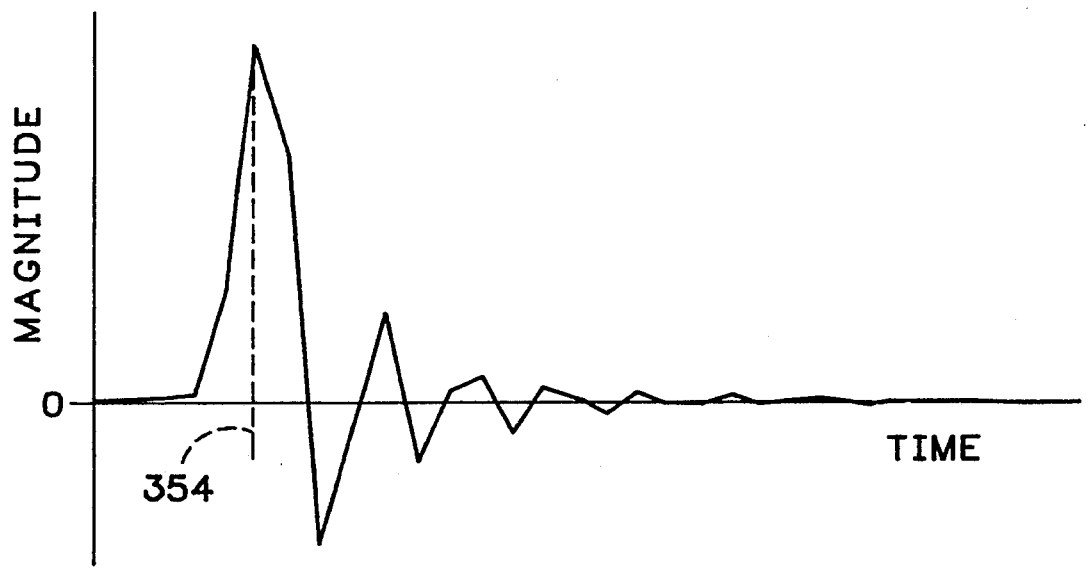
FIG. 20 is an illustration of a first impulse extracted from the impulse response signals of FIG. 18B.
Figure 22:
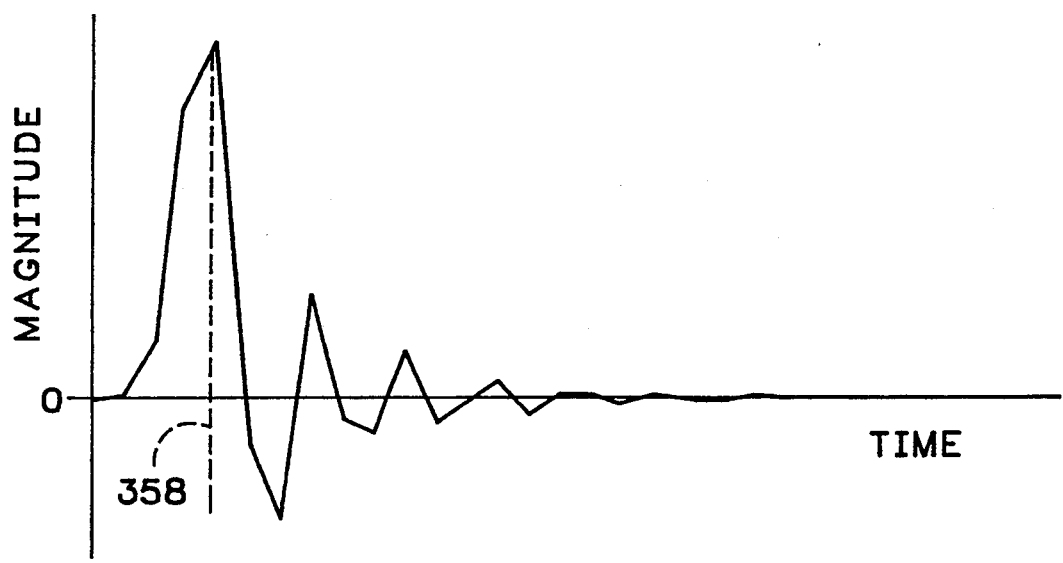
FIG. 22 is an illustration of a second impulse extracted from the impulse response signals of FIG. 1813.

The second impulse is phase shifted with the phase correction ramp in block 344. The phase shifted second impulse is then summed with the first impulse in block 346. If the number of extracted impulses has not reached a predetermined limit, decision block 348 returns to the impulse extraction process in block 336. Upon extracting and summing a predetermined number of characterization impulses, decision block 348 jumps out of the pulse extraction loop and an inverse fast Fourier transform (IFFT) of the averaged impulse is performed in block 350. To further explain, FIG. 20 illustrates a first impulse extracted from the impulse response signals of FIG. 18 (impulse 326). A positive peak occurs at location 354 on the time axis and would therefore be marked in block 330 (FIG. 19). FIG. 22 illustrates a second impulse extracted from the impulse signals. The positive peak magnitude occurring at location 358 was also marked in block 330 (FIG. 19).

Figure 21:
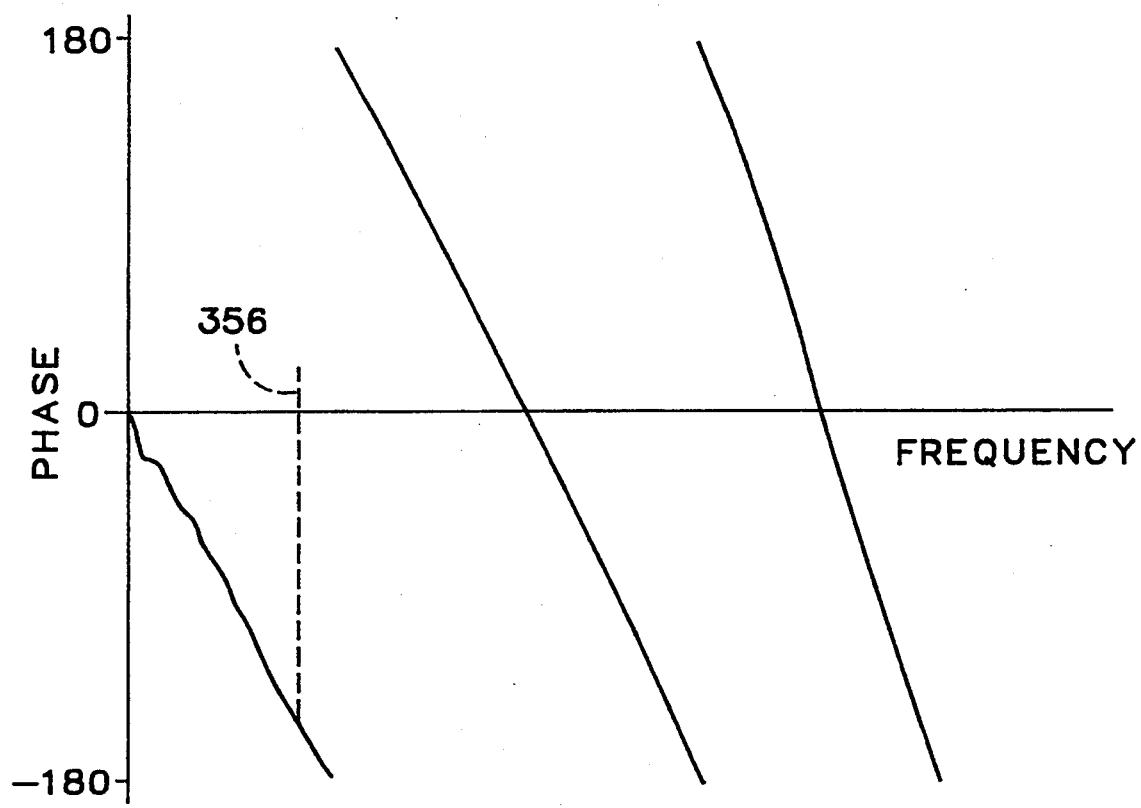
FIG. 21 and 23 illustrate the phase response of the first and second extracted impulses respectively.
Figure 23:
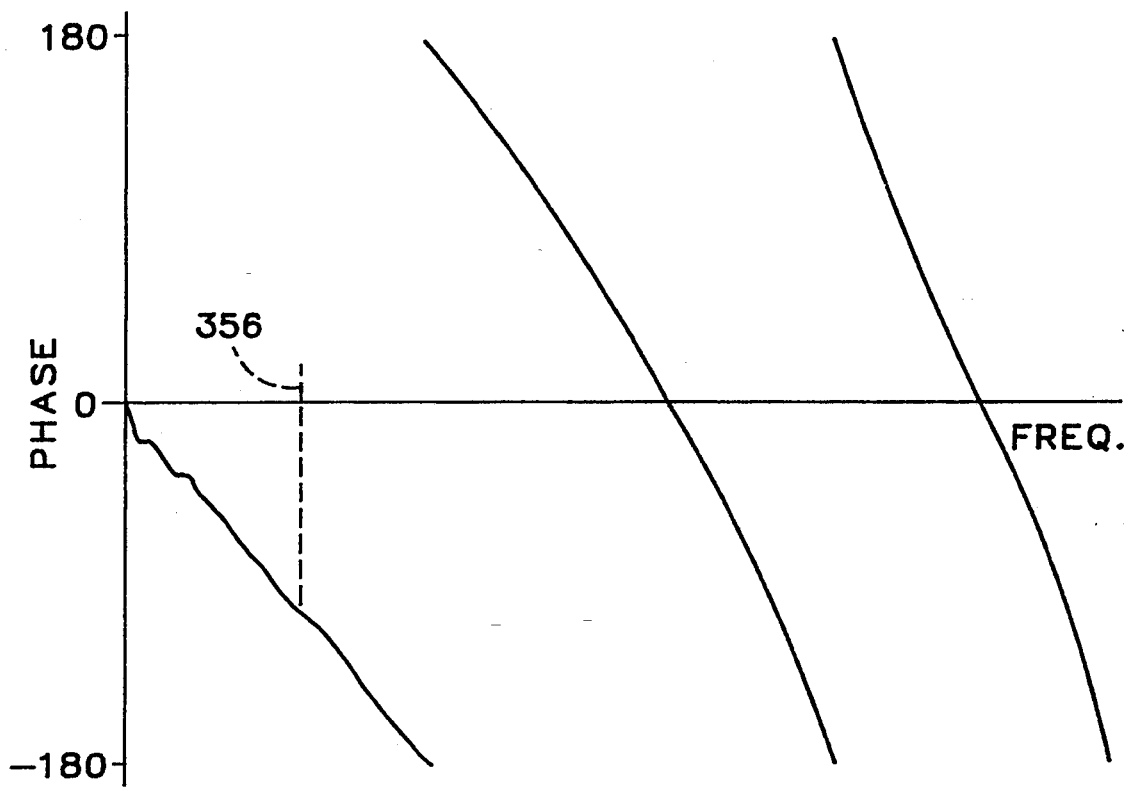

The frequency response of the two extracted impulses are generated in FFT block 338 (FIG. 19). FIG. 21 and 23 illustrate the phase response of the first and second impulse respectively. Referring back to FIG. 19, block 340 first determines the phase of the first impulse at a predetermined reference frequency (e.g. sample point 356 in FIG. 21 ). The reference frequency is selected at a discrete frequency bin in the FFT output.

Compute phase correction block 340 next determines the phase of the second impulse at the same reference frequency (e.g. sample point 356 in FIG. 23). The phase difference between the first impulse and the second impulse is used in block 342 to create a phase correction ramp. The ramp is a complex vector with a magnitude equal to 1 that has a slope equal to the phase difference between the first impulse and the second impulse. The phase ramp is multiplied with the frequency response of the second impulse. This aligns the second impulse with the first impulse. The second phase shifted impulse is then summed in block 346 with the first impulse.

Decision block 348 then returns to block 336 where the next impulse from the impulse train is extracted in block 336. Each additional impulse is aligned with the first impulse and summed with the previously aligned impulses. The process continues until a predetermined number of characterization impulses have been aligned and summed. The impulse average is then generated by scaling the impulse sum by the total number of extracted impulses. The impulse average is transformed back into the time domain in block 350.

The accuracy of impulse phase shifting is improved significantly by choosing a reference frequency at a discrete frequency bin in the FFT output. For example, if the impulse phase is calculated at an arbitrary frequency, the accuracy of the phase measurement will be limited by the sampling resolution, i.e., the time period between two adjacent samples. However, selecting a frequency that falls on an FFF bin for measuring the reference frequency allows an accurate phase measurement that is independent of the sample rate. The accuracy of the phase measurements are therefore only limited by the word length of the processing system. Processing complexity is also reduced since interpolation is not required.

FIGS. 24 and 25 illustrate the effects of averaging on an impulse response signal. FIG. 24 illustrates a "noisy" impulse from the impulse signal illustrated in FIG. 18. Random noise was intentionally introduced while recording the impulse signals. FIG. 25 illustrates an average of 300 impulse responses. The random noise in the impulses has been reduced significantly providing a more accurate characterization of the recorder/playback unit.

Although the foregoing method for averaging impulse responses is operative, it is not preferred. The technique for statistically selecting and averaging step responses explained in the following Section 9 is preferred for both impulse and step response characterization of the ECG recorder and playback system.

7. Impulse Response Integration

Due to differentiation effects occurring during tape playback, the impulse response needs to be integrated. The integration must be performed with two important constraints: the integration must have no DC gain and the phase shift must be sufficiently linear down to the lowest frequency of interest. In order to meet these constraints, a forward and backward filtering technique is used.

Figure 26:
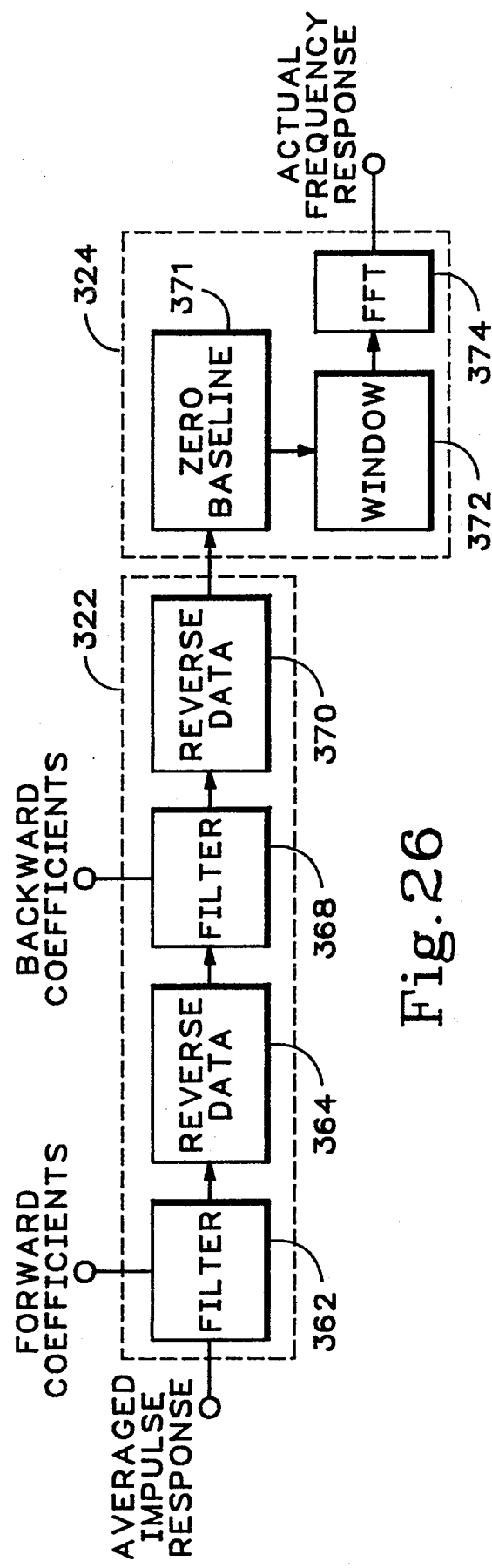
FIG. 26 is a detailed block diagram of the integration block and the FFT block of FIG. 17.

Referring to FIG. 26, dashed box 322, is a detailed illustration of the integration block 322, in FIG. 17, and dashed box 324 is a detailed illustration of FFT block 324 in FIG. 17. The averaged impulse response generated in block 320 (FIG. 17) is fed into a first infinite impulse response filter (forward IIR filter) in block 362 along with a set of forward filter coefficients. The forward filtered data is reversed in block 364 and fed along with a set of backward filter coefficients into a second IIR filter (backward IIR filter) in block 368. The impulse data is then reversed back into to a forward time sequence in block 370. The impulse data is adjusted for zero baseline in block 371, windowed in block 372, and transformed into the frequency domain by FFF block 374. The FFT output is referred to as the actual frequency response.

Discrete time implementations of the forward and backward filters are used as opposed to analog filters for higher reliability and easier realization of tight frequency-domain specifications. IIR filters are used as opposed to FIR filters to provide sharp frequency response with a relatively small filter size. The second IIR filter in conjunction with reversing the data corrects for the nonlinear phase response of the first IIR filter. In addition, the second filter has one zero at DC and two poles which provide a 90° phase shift compensating for the playback head differentiation.

The forward IIR filter in block 362 can be either a single or multiple pole integrator. For filter stability, all the poles must reside within the Z-plane unit circle. The IIR filter in backward filter block 368 is the same filter as the IIR filter in forward filter block 362 only with an additional zero added at DC (i.e., $Z=1$). The forward filter has either 0 or 1 zeroes at DC, therefore, its numerator must either be 1 or $(1-Z^{-1})$. The backward filter has either 1 or 2 zeroes at DC, so its numerator is either $(1-Z^{-1})$ or $(1-Z^{-1})(1-Z^{-1})=(1-2Z^{-1}+Z^{-2})$. The denominators for the forward and backward filters are equal, each having one or two poles that lie within the unit circle. The transfer functions for a first order forward/backward IIR filter scheme are therefore as follows:

$$H_1(Z)=1/(1-aZ^{-1}); \text{ and}$$

$$H_2(Z)=(1-Z^{-1})/(1-aZ^{-1}),$$

where $H_1(Z)$ is the transfer function of the forward IIR filter and $H_2(Z)$ is the transfer function of the backward IIR filter.

Figure 27:
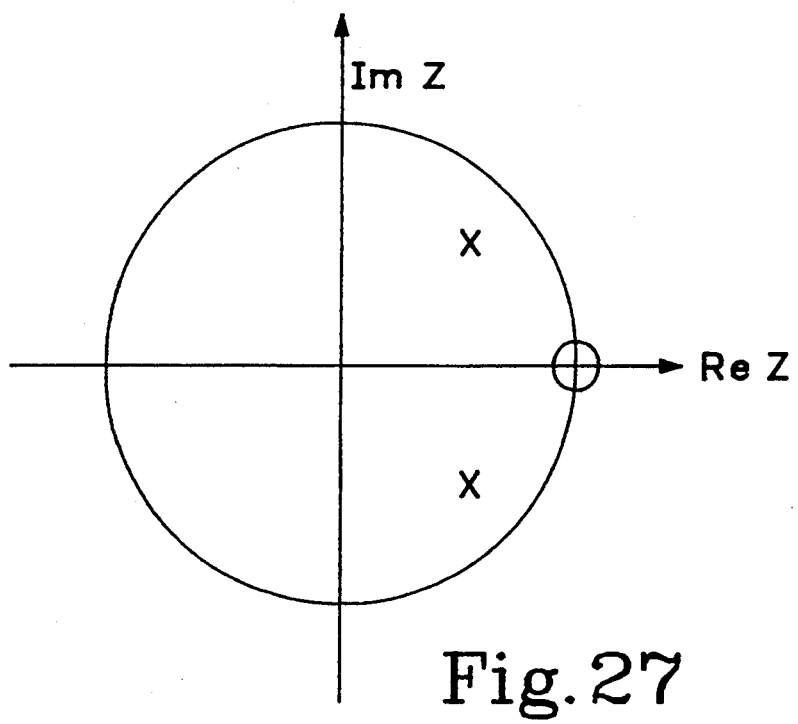
FIG. 27 illustrates the locations of the poles and zeros within the Z-plane for a forward IIR filter.
Figure 28:
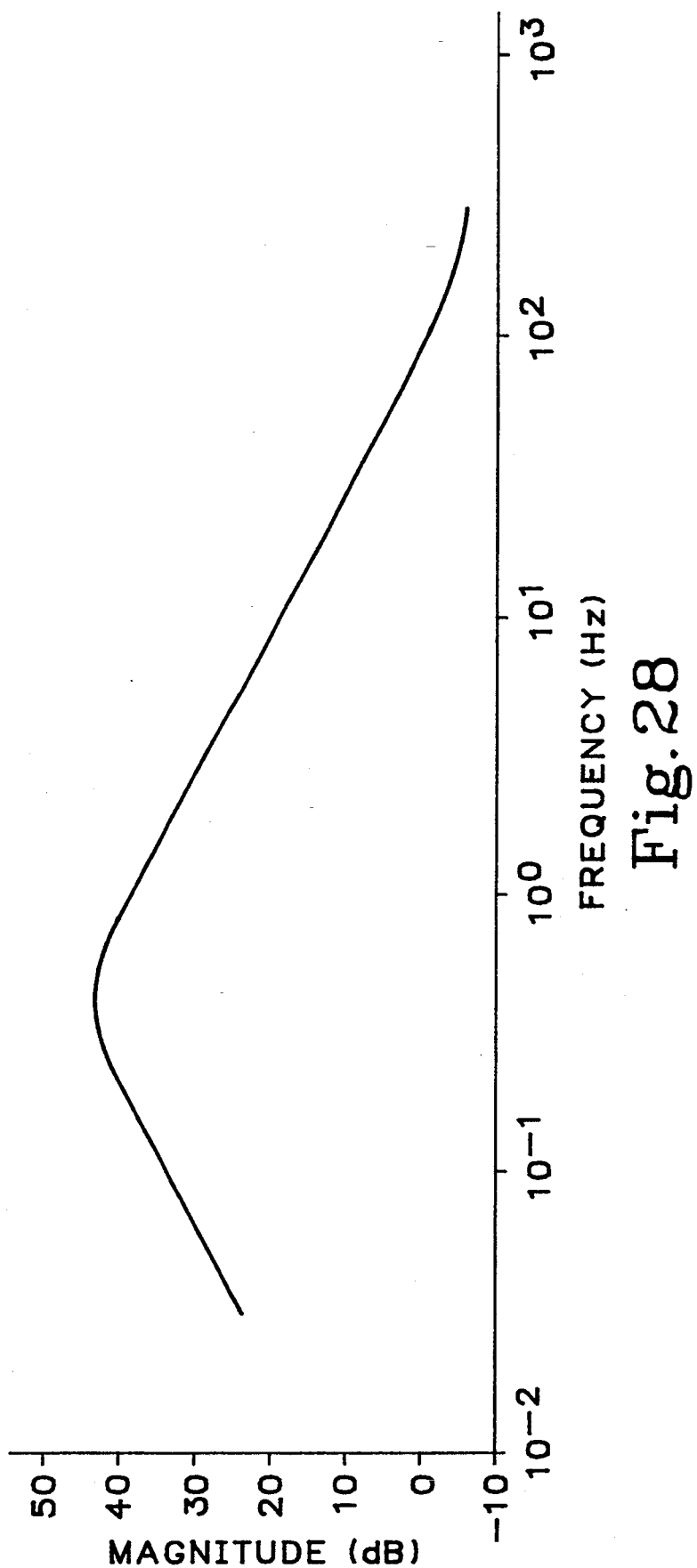
FIGS. 28 and FIG. 29 illustrate the magnitude and phase response respectively for the forward IIR filter used in implementing the invention.
Figure 29:
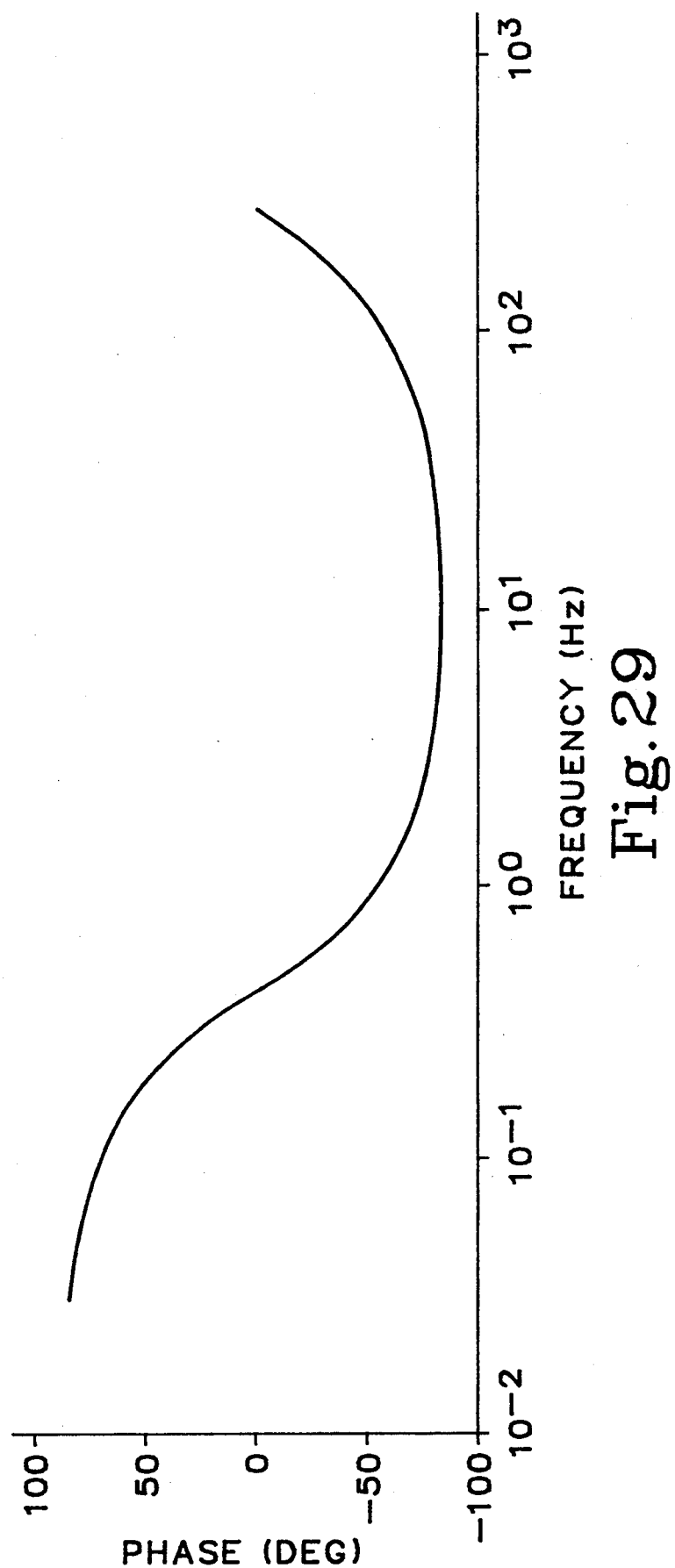

FIG. 27 illustrates the locations of the poles and zero within the Z-plane for the second order forward IIR filter. A single zero occurs at one and two poles occur within the unit circle. FIG. 28 and FIG. 29 illustrate the magnitude and phase response respectively for the forward IIR filter. As illustrated in FIG. 28, the forward IIR is a band pass filter with a peak occurring at a relatively low frequency. However, as illustrated in FIG. 29, the phase response of the forward IIR filter is nonlinear at low frequencies.

Figure 30:
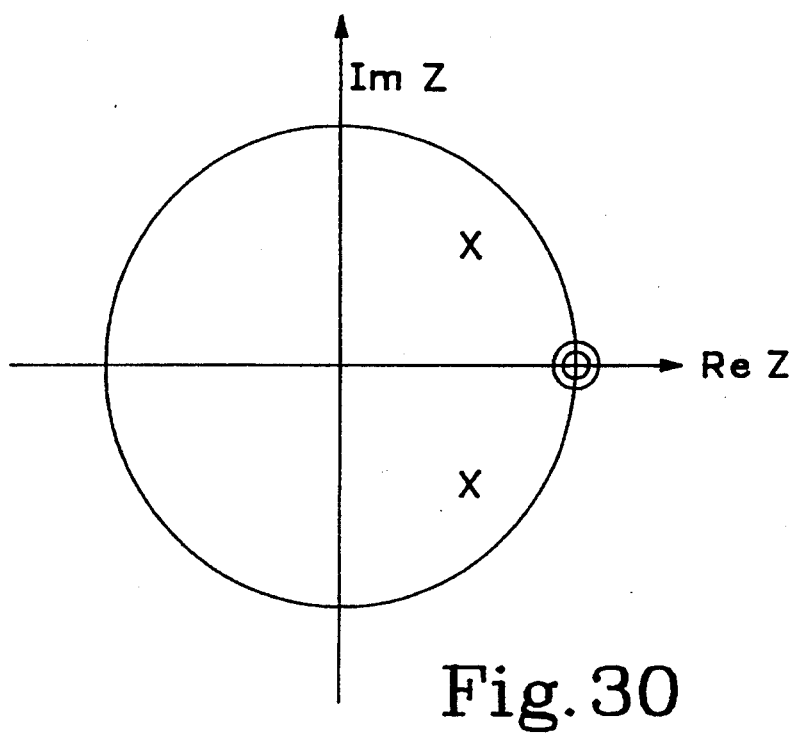
FIG. 30 illustrates the locations of the poles and zeros within the Z-plane for a reverse IIR filter used in implementing the invention.
Figure 31:
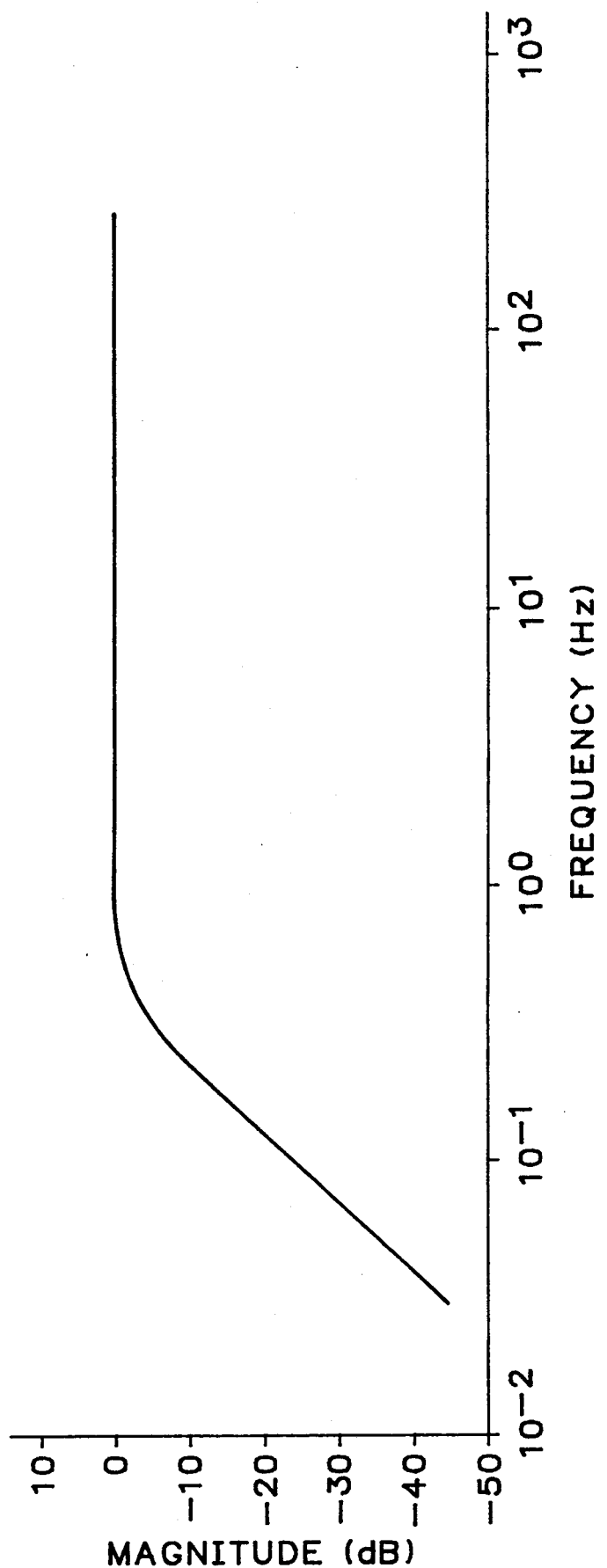
FIGS. 31 and 32 illustrate the magnitude and phase response respectively for the reverse IIR filter.
Figure 32:
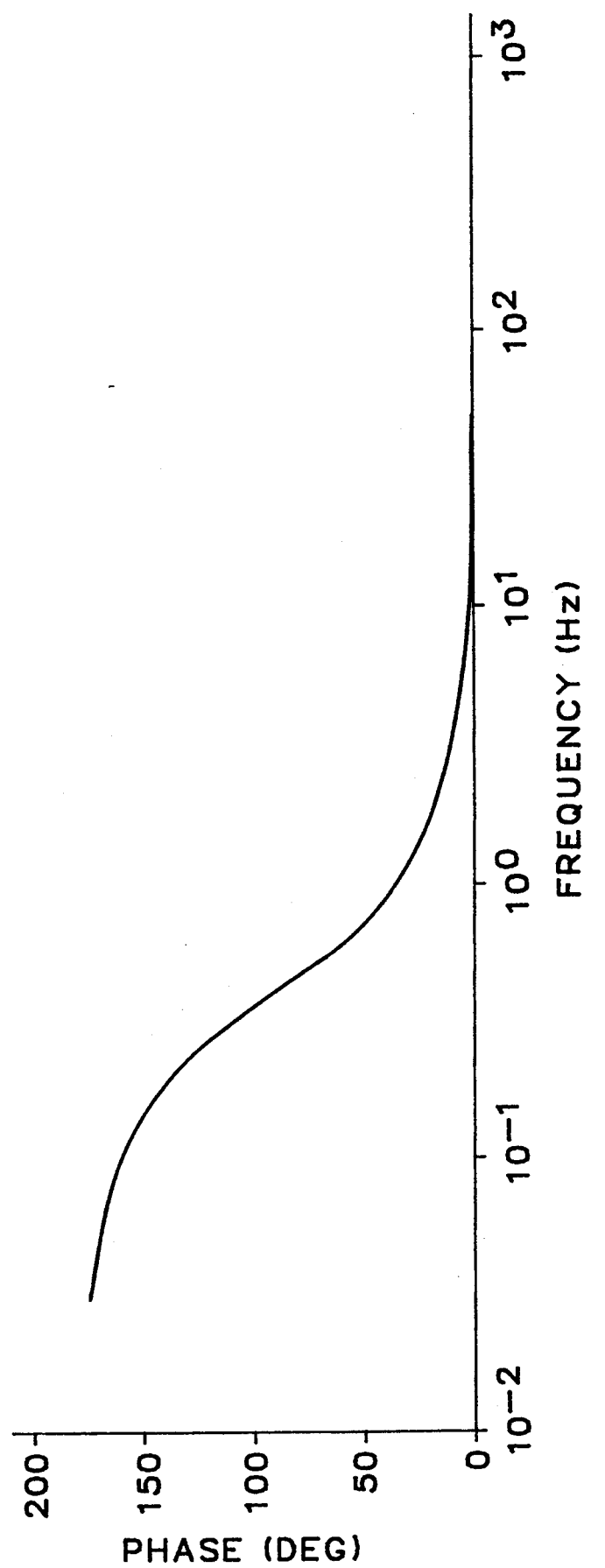

FIG. 30 illustrates the locations of the poles and zero within the Z-plane for the backward IIR filter. The two poles occur at the same locations as the poles of the forward IIR filter. A high pass filter is created, however, by adding a second zero at zero. FIGS. 31 and 32 illustrate the magnitude and phase response respectively for the backward IIR filter. The magnitude response of the backward filter adds additional rolloff at low frequencies to reduce DC gain. The phase response of the backward IIR filter in FIG. 32 is complementary with the forward IIR phase response in FIG. 29 and is offset by 90 degrees.

Figure 33:
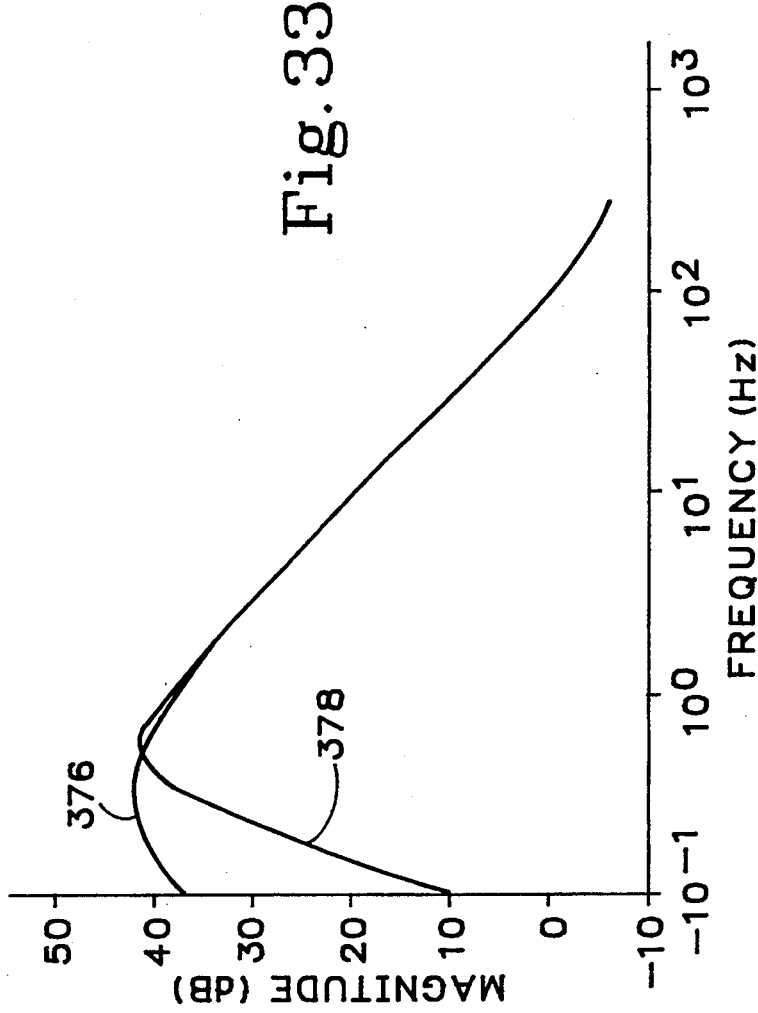
FIG. 33 is an illustration of the overall magnitude response of the forward-reverse IIR filter.

FIG. 33 illustrates the overall magnitude response of the forward and backward IIR filtering process. The forward and backward IIR filtering process results in a band pass integrator with no gain at DC and a linear phase response. As explained above, the bandpass filter can be either a first order integrator (curve 376) or a second order integrator (curve 378). Unlike a forward only IIR filter, this implementation introduces no phase distortion and enables the integrator peak to be positioned much closer to the desired low frequency cutoff value. The higher peaking frequency response of the forward and backward IIR filter allows minimum amplification of low frequency noise, thereby reducing baseline wander.

Referring back to FIG. 26, after the impulse response has been integrated (dashed block 322) it is adjusted to minimize baseline offset in block 372. This is necessary so that the actual frequency response matches a desired frequency response (DFR). Since the DFR is typically specified as a low pass function, its impulse response has a baseline with zero offset. To estimate the baseline offset, the mean of a predetermined number of samples at the beginning and at the end of the impulse are computed. The mean of the samples define an offset value that is subtracted from the impulse.

The impulse is also windowed in block 372 to reduce leakage. A fast Fourier transform (FFT) of the windowed impulse response is performed in block 374. The length of the FFT in block 374 is sufficient to capture the entire integrated pulse. The output of FFT block 374 is defined as the actual frequency response of the recorder and playback unit and is used to generate the correction filter coefficients. The windowing and FFT performed in blocks 372 and 374 are standard techniques known to those skilled in the art.

8. Overview of System Characterization Using a Step Response

Preferably, the system is characterized using a step response rather than an impulse response as described above. In the impulse process described above, the impulse response must be integrated to return the impulse to its original undifferentiated state. However, differentiating a step signal creates an impulse signal. Therefore, if a step signal is used to characterize the recorder and playback unit, there is no need to integrate the output response. In other words, use of a step signal without the integration step used in the impulse characterization provides an impulse response. Use of a step signal is also advantageous in that it contains more low frequency energy than an impulse signal. This provides more effective characterization of the recorder and playback unit at low frequencies.

Figure 34:
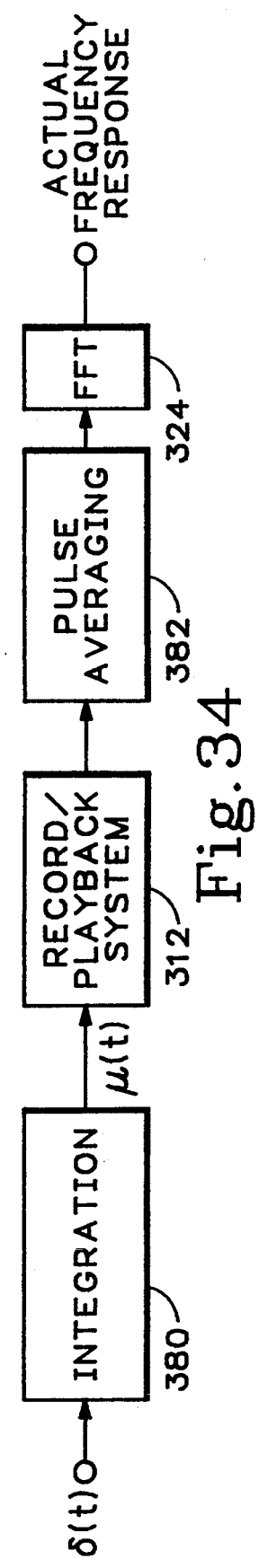
FIG. 34 is a block diagram illustrating a process for characterizing the frequency response of a recorder and playback unit with a step signal.

FIG. 34 is a block diagram illustrating a process for characterizing the recorder and playback unit with a step signal. An impulse signal $\delta(t)$ is integrated in block 380 generating a step signal $u(t)$. The step signal $u(t)$ is used as the input characterization signal for the recorder and playback unit 312. The step response signal played-back from system 312 is again averaged in a pulse averaging block 382 to remove random noise. The averaged pulse response is then adjusted for zero baseline, windowed, and Fourier transformed in a similar manner as shown in block 324 (FIG. 26). The output of block 324 is the actual frequency response of the recorder and playback unit. The step signal output from block 380 is produced by generating a rectangular pulse and removing the effects of its falling edge in the step response signal. Alternatively, if present, calibration pulses can be used for the step signal.

9. Step Response Averaging

Figure 35:
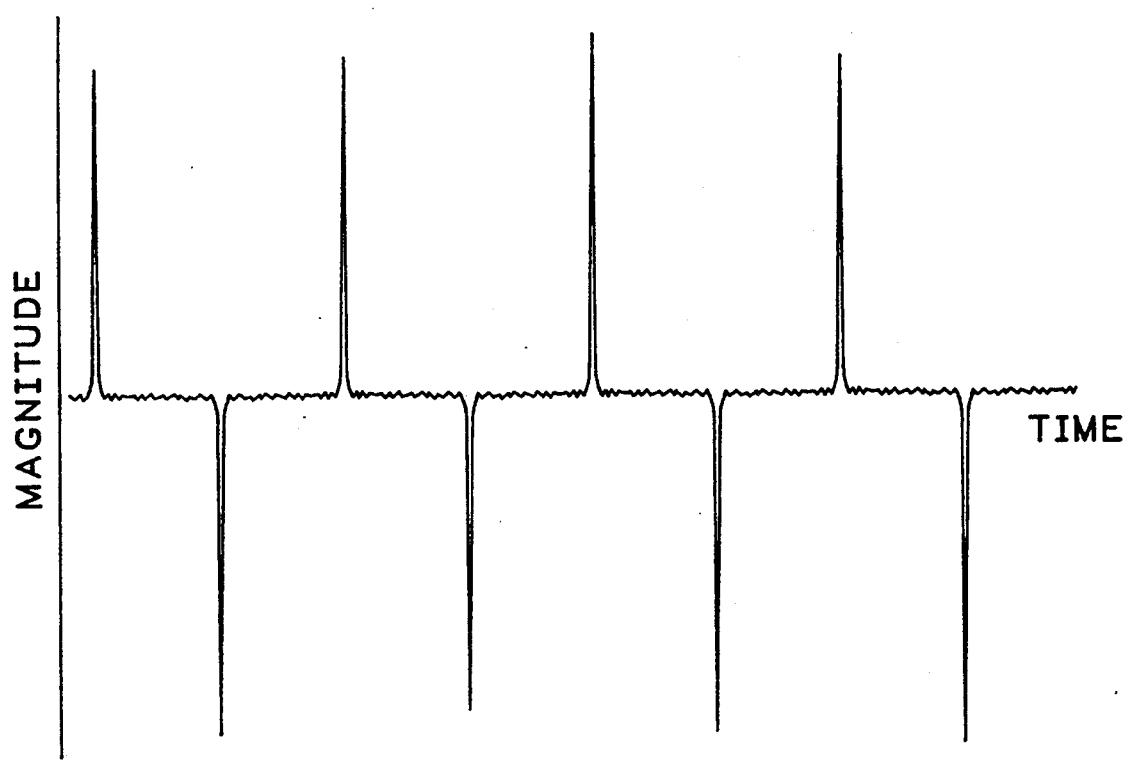
FIG. 35 is an illustration of the step response signal from the recorder and playback unit.
Figures 36, 37:
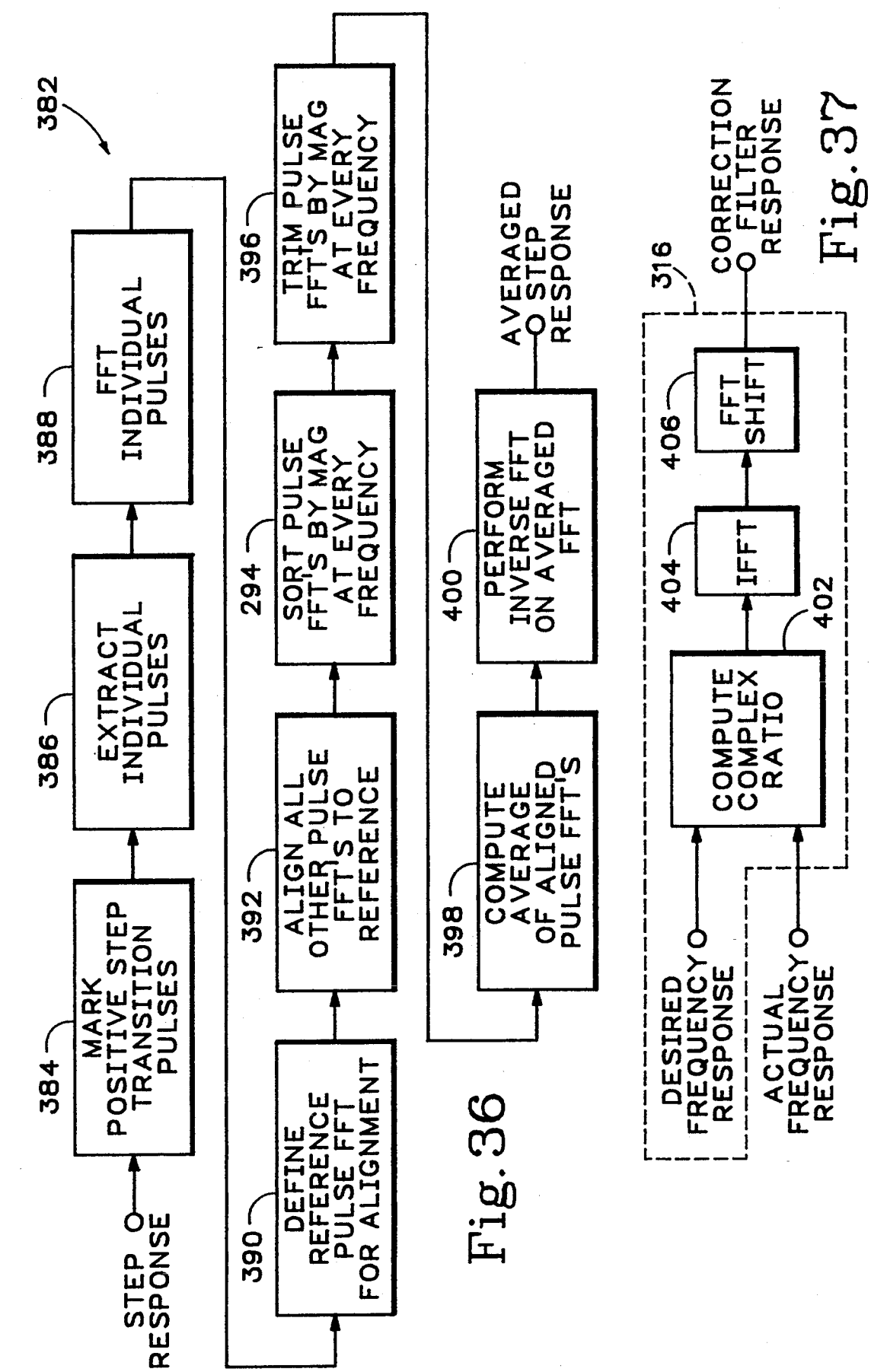
FIG. 36 is a detailed block diagram of the pulse averaging block 382 of FIG. 34.
FIG. 37 is a detailed block diagram of the correction filter generation block 316 of FIG. 15.

FIG. 35 is the step response signal output from the recorder and playback unit. The positive and negative pulses are generated by the rising and falling edges respectively of a rectangular pulse. FIG. 36 is a detailed block diagram of the pulse averaging block 382 from FIG. 34. This averaging process is an alternative to the impulse averaging method illustrated in FIG. 19. The pulse averaging method provides additional pulse rejection processing that further reduces noise and signal drop-out effects from the step response signal.

The position of each positive step transition in the step response (FIG. 35) is marked in block 384. The positive pulses are extracted from the step response signal and organized into a pulse matrix in block 386. Each extracted pulse is windowed and Fourier transformed in block 388. A reference pulse index is selected from the extracted impulses in block 390. The reference pulse index, the alignment frequency, and the sampling frequency are used in block 392 to create an aligned FFT matrix from the pulse matrix. Once all of the pulses have been aligned they are sorted and trimmed according to their magnitudes in blocks 394 and 396 respectively. The trimmed matrix is converted into an averaged FFT pulse matrix in block 398 and transformed in IFFT block 400 to produce the averaged system impulse response.

In marking the positive step transitions within the step response signal, raw step positions can be derived from a standalone rectangular pulse input signal or from a rectangular pulse signal derived from calibration pulses (see FIG. 18). As described previously, the specific spacing between the positive and negative transitions of the step response input signal allow the characterization rectangular pulse input signal to be identified and extracted from a calibration signal. Alternatively, a single square wave signal can be provided for use as both a characterization and calibration signal.

Block 384 defines a minimum threshold for peak position identification. The threshold is based on the peak values of the raw data. To minimize picking a spurious peak as the peak value, the entire step response signal, which includes a plurality of individual step responses, is split into eight groups, and the maximum value of each step response in each group is computed. This group of maximum values is then sorted in ascending order. The highest and lowest maximums are discarded, and 30% of the mean of the remaining maximum values becomes the minimum threshold. Corresponding peak positions above the threshold are then identified. Since a cluster of peak positions are identified for each pulse transition, block 384 pares each "peak cluster" down to one peak.

Once the peak positions have been defined, the step pulses are identified, extracted, and stored in a pulse array in block 386. A FFT is computed in block 388 for the pulse array. The pulses are then aligned with a reference pulse. Block 390 selects a reference pulse that resides at the center of a magnitude response distribution at a predetermined alignment frequency. The alignment process in block 392 then determines the difference in phase between the reference pulse and each unaligned pulse at the alignment frequency. The phase difference is then tested and corrected for phase wrap beyond $+/-\pi$. A phase correction ramp is created from the phase difference that passes through 0° at DC and the phase difference value at the sampling frequency. The ramp is used to create a complex phase correction vector that is multiplied with the FFT of the unaligned pulse.

To further eliminate the effects of signal dropouts and noise, blocks 394 and 396 statistically trim data that is outside a predetermined signal level. Block 394 first ranks the pulse magnitudes at each frequency in ascending order. Block 396 then trims the lowest and highest percentage of magnitudes at each frequency. The remaining values at each frequency are averaged to produce a trimmed mean at each frequency. The remaining aligned pulses are then averaged in block 398, and transformed back into the time domain in block 400. Referring back to FIG. 34, the averaged step response from block 382 is processed in block 324 to generate the actual frequency response. A zero baseline offset, windowing, and Fourier transform process are performed in block 324 in the same manner as that illustrated in block 324 of FIG. 26.

As mentioned above in Section 6, Impulse Response Averaging, the system described in this section for statistically selection and averaging of step responses is the preferred system for selecting and averaging impulse responses.

10. Generating a Correction Filter Based on an Impulse or Step Response

A correction filter response, i.e., digital correction filter coefficients, is derived from the combined recorder and playback frequency response and a predetermined desired response. The correction filter, when applied to the ECG data, effectively flattens the magnitude response and linearizes the phase response of the recorder and playback unit within a desired frequency band (e.g. 0.67 Hz to 100 Hz). A finite impulse response (FIR) filter is used to apply the correction filter coefficients to the played-back patient ECG data.

FIG. 37 is a detailed block diagram of the correction filter generation block 316 of FIG. 15. The predetermined desired frequency response D(k) and the actual frequency response H(k) are fed into compute complex ratio block 402. As described above, the actual frequency response can be derived from either the recorder and playback impulse response (see FIG. 17) or step response (see FIG. 34). The correction filter response from block 402 is transformed into the time domain by IFFT block 404. The transformed correction coefficients are shifted in block 406 to generate the correction filter coefficients a(i).

The desired system frequency response of the recorder and playback unit is determined by the signal characteristics of the patient ECG data. For example, the majority of information in ECG data occurs within the frequency range between 0.67 and 100 Hz. Therefore, the desired frequency response is generated to specifically emphasize data within this frequency range and frequencies outside this frequency range are removed. However the desired frequency response can be changed to emphasize specific ECG frequency components inside or outside the above mentioned frequency range.

Figures 38, 39:
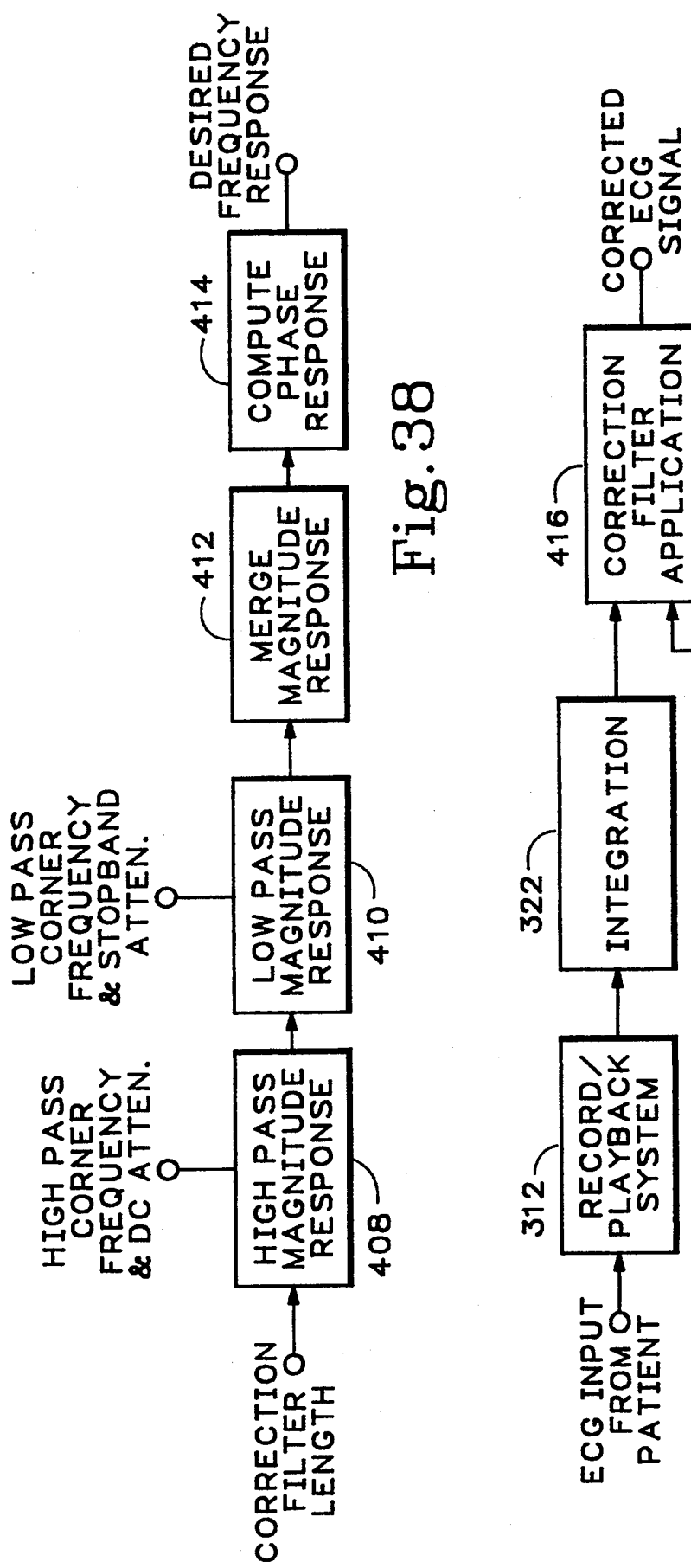
FIG. 38 is a detailed block diagram illustrating a process for generating a desired frequency response.
FIG. 39 is a block diagram illustrating a process for applying the connection filter to played-back patient ECG data.

FIG. 38 is a detailed block diagram illustrating the process for generating the desired frequency response. The correction filter length, high pass corner frequency, DC attenuation, low pass corner frequency and stopband attenuation values are predetermined parameters. The desired high pass magnitude response is derived in block 408. The high pass parameters control the location of the forward and backward integrator's filter peak and the system's low frequency performance. If the stop band is specified to be greater than −3 dB, no special rolloff is assumed and the high pass magnitude is set to one.

The low pass portion of the desired magnitude response is generated in block 410. The predetermined low pass parameters define the system's upper bandwidth. The high and low portions of the desired magnitude response are multiplied together in block 412 to generate the desired magnitude response. To minimize overshoot and ringing in the time domain magnitude transition bands for the high pass and low pass filter sections are created by fitting the pass and stop bands with a Gaussian rolloff. The method of generating a Gaussian rolloff is known to those skilled in the art.

The desired phase response is created based on the length of the FIR correction filter. It assumes that a linear phase response corresponds to a phase accumulation of 180 degrees across each filter tap. A phase ramp is then generated that defines a desired phase response that results in a correction filter with a symmetrical IFFT. The phase and magnitude response are merged in block 414, creating a complex array that represents the desired frequency response. The array is then fed into compute complex ratio block 402 (FIG. 37).

Referring back to FIG. 37, the ratio of the desired frequency response and the actual frequency response are computed for each frequency from DC to the sampling frequency in block 402. As described earlier, the correction filter magnitude response is generated by taking the ratio between the desired magnitude response and the actual frequency response. For example, the correction filter magnitude response $||B(k)||$ is derived by taking the ratio between the actual magnitude response $||H(k)||$ and the desired magnitude response $||D(k)||$ as follows:

$$||B(k)|| = \sim D(k)||\,/\,||H(k)||.$$

If the magnitude of the desired frequency response is 1, the correction filter magnitude response is simply the inverse of the actual magnitude response as follows:

$$||B(k)|| = 1/\,||H(k)||.$$

The correction filter phase response B(k) is generated by summing the phase of the actual frequency response H(k) with the phase of the desired frequency response phase D(k), as follows:

$$B(k) = D(k) - H(k)$$

After the magnitude mid phase coefficients are computed, the correction filter is transformed into the time domain by inverse fast Fourier transform (IFFT) block 404. The next step is an FFT shift which moves the zeroth lag to the center of the spectrum.

FIG. 39 is a block diagram illustrating how the correction filter is applied to played-back patient ECG data. Patient ECG data is recorded by the recorder and playback unit 312. The ECG data is played-back from system 312 then integrated in block 322. The integration method performed in block 322 is the same forward and backward filter scheme used in integrating the recorder and playback impulse response (see FIG. 26). An FIR filter is used to apply the correction filter coefficients to the integrated patient ECG data in block 416. The FIR filter coefficients correct for the attenuation and nonlinear characteristics in the magnitude and phase response of the recorder and playback unit. This increases the effective bandwidth of the recorder and playback frequency response, in turn reducing frequency-response induced distortion in the played-back patient ECG data.

11. Real Time Implementation of Correction and Integration Filters

The process used to integrate patient ECG data in block 322 and to correct the patient ECG data in block 416 involve three filters. The integration process uses a forward IIR filter and a backward IIR filter, and the correction process uses a FIR filter. The filters are described as follows:

$$H_1(Z) = 1/(1 - aZ^{-1});$$

$$H_2(Z) = (1 - Z^{-1})/(1 - az^{-1});\text{ and}$$

$$H_3(Z) = b_0 + b_1 Z^{-1} + b_2 Z^{-2} + \ldots + b_M Z^{-M},$$

where $H_1(Z)$ has previously been referred to as the forward IIR filter, $H_2(Z)$ has previously been referred to as the backward IIR filter, and $H_3(Z)$ has previously been referred to as the FIR filter. To reduce computational requirements and enable application of the filtering techniques on real-time continuous data, $H_2(Z)$ and $H_3(Z)$ are combined to produce one forward IIR filter referred to as $H_f(z)$. The IIR filter $H_1(Z)$ remains the same but is now referred to as $H_r(z)$.

The forward IIR filter is created from the multiplication of $H_2(z)$ and $H_3(z)$. The forward IIR filter numerator polynomial coefficients (B) of length M+1 are computed by convolution as follows:

$$[B_0 B_1 \ldots B_{M+1}] = [1 -1] \; [b_0 b_1 \ldots b_M]$$

This places the extra zero in the forward filter rather than the reverse filter as previously described. The denominator is the same as the denominator of $H_1(Z)$ or $H_2(Z)$. Consequently, the forward IIR is as follows:

$$H_f(z) = (B_0 + B_1 Z^{-1} + B_2 Z^{-2} + \ldots + B_{M+1} Z^{-(M+1)})/(1 - aZ^{-1}).$$

The backward IIR is simply the previously defined forward IIR $H_3(Z)$:

$$H_r(Z) = H_3(Z) = 1/(1 - aZ^{-1}).$$

Placing the extra zero in the forward IIR rather than the reverse IIR adds only one multiply to each forward pass, and allows more efficient coding. The effect of $H_f(z)$ and $H_r(z)$ is the same as that of $H_1(Z)$, $H_2(Z)$ and $H_3(Z)$, with an additional 180° phase shift. This difference is equivalent to multiplying by $-1$. The forward IIR is passed across the played-back patient ECG data point by point as it is acquired. Reverse filtering in real time requires that the data filtered by $H_f(z)$ be collected into overlapping blocks of length $L+dL$ before $H_r(z)$ can be passed across it, where L is the filter length and dL is the overlapped filter settling time. The output from filtering the first dL points are thrown out because it contains erroneous transient responses, while the output from the remaining L points is passed on to the buffer RAM.

Figures 40, 41, 42:
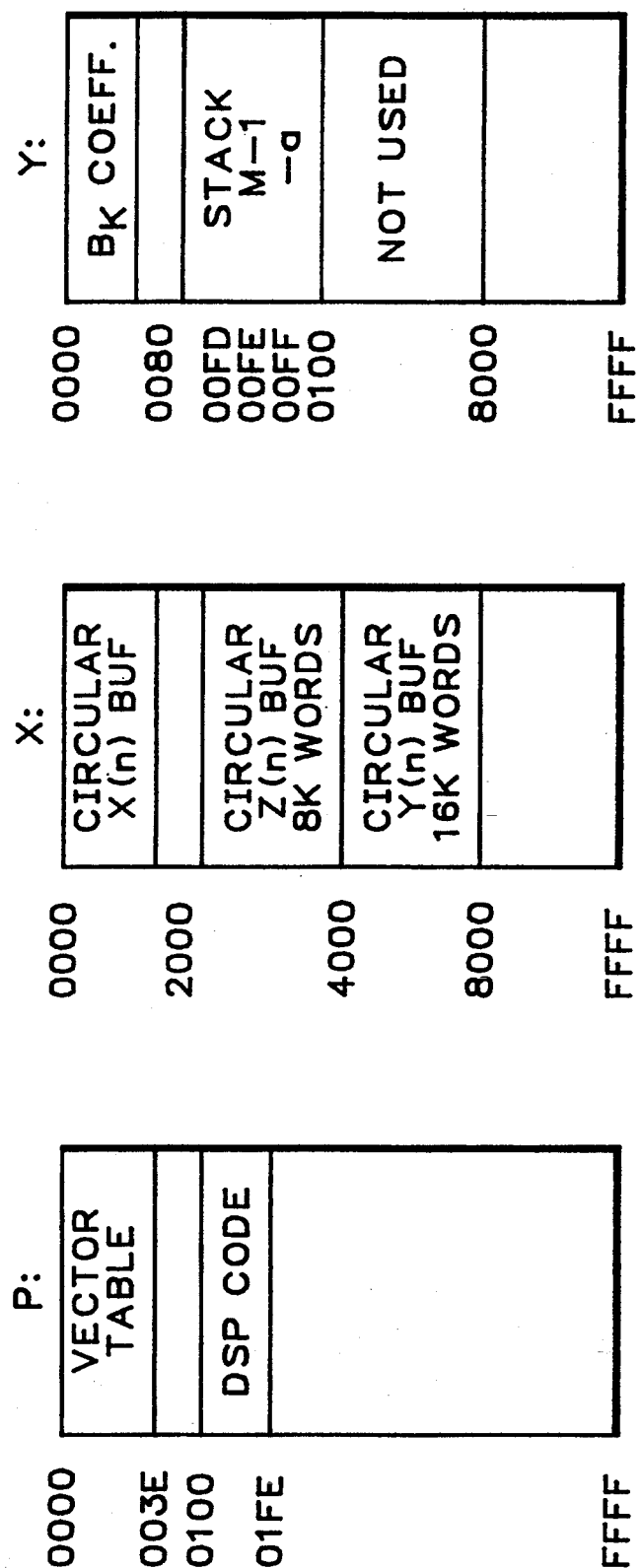
FIGS. 40, 41, and 42 illustrate a memory mapping scheme for filtering patient ECG data.

FIGS. 40, 41, and 42 illustrate a memory mapping scheme for the real-time filtering implementation described above. A typical DSP that is used to implement the filtering process is the Motorola 56002. A single DSP can be implemented or for faster processing a separate DSP can be used to process the patient ECG data for each channel. Memory space P in FIG. 40 is used for storing DSP code and associated filter vector information.

Raw data comes into the DSP sample by sample through an I/O port. Each sequential sample is placed at the top of a continuously revolving X(n) buffer as illustrated by memory space X in FIG. 41. The length of the X(n) buffer is equal to the number of coefficients in the forward IIR numerator. As each sample point enters the DSP, it is passed through the forward IIR filter and the result placed at the top of a continuously revolving 16K word circular buffer Y(n) within memory space X. Y(n) is calculated as follows:

$$Y(n) = B_0 X(n) + B_1 X(n-1) + \ldots + B_{M+1} X(n-M+1) + aY(N-1),$$

where Y(n) is the input-output relationship for the forward IIR filter $H_f(Z)$. The forward filter coefficients $B_K$ are stored in memory space Y as illustrated in FIG. 42. Periodically, as the Y(n) buffer fills to the length $L+dL=8K+2K$, the DSP passes the backward IIR filter over the entire 10K block and saves the last 8K into the circular Z(n) buffer of memory space X. Z(n) represents the input/output relationship for the backward IIR filter and is calculated as follows:

$$Z(-n) = Y(-n) + aZ(-n+1).$$

The variable $-n$ represents outputs from the forward IIR in reversed order. After an entire 8K block of impulse data is filtered, it is output to the buffer RAM, and the process is repeated with another L+dL data block. The process continues until all patient ECG data has been corrected.

12. Effect of Correction and Integration Filters

Consideration will now be given to the magnitude response of a correction filter derived as described above and the magnitude response of a system for recording and playing back ECG signals with and without the filter. Also illustrated is the group delay for the system after application of the filter.

Figure 43:
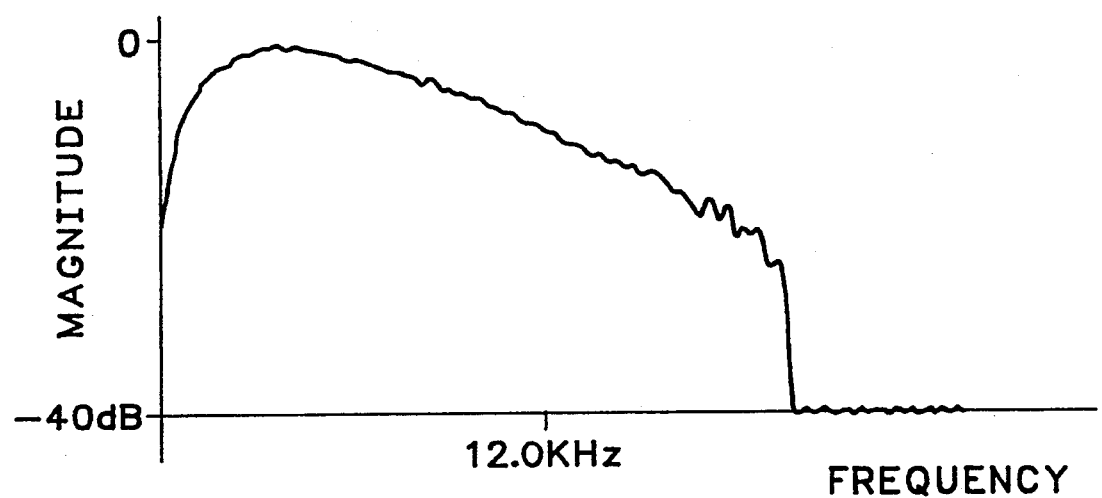
FIG. 43 is the magnitude response of the recorder and playback unit of FIG. 11.
Figure 44:
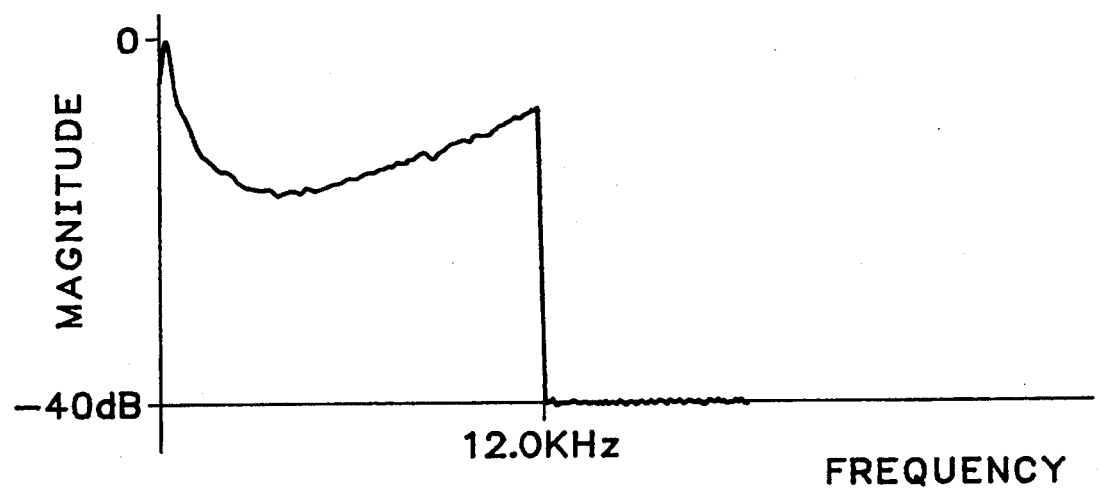
FIG. 44 is an illustration of the magnitude response of the correction filter.

FIG. 43 is the magnitude response of the recorder and playback unit previously illustrated in FIG. 1 without implementation of a correction and integration filter as described above. FIG. 44 illustrates the magnitude response of a combined correction and integration filter generated as described above. It is evident from FIG. 44 that within the frequency band from 0.15 Hz to 100 Hz (12.0 kHz/120), the correction filter has a magnitude response that is the inverse of the recorder and playback magnitude response. At frequencies greater than 100 Hz, the magnitude response of the correction filter is attenuated.

Figure 45:
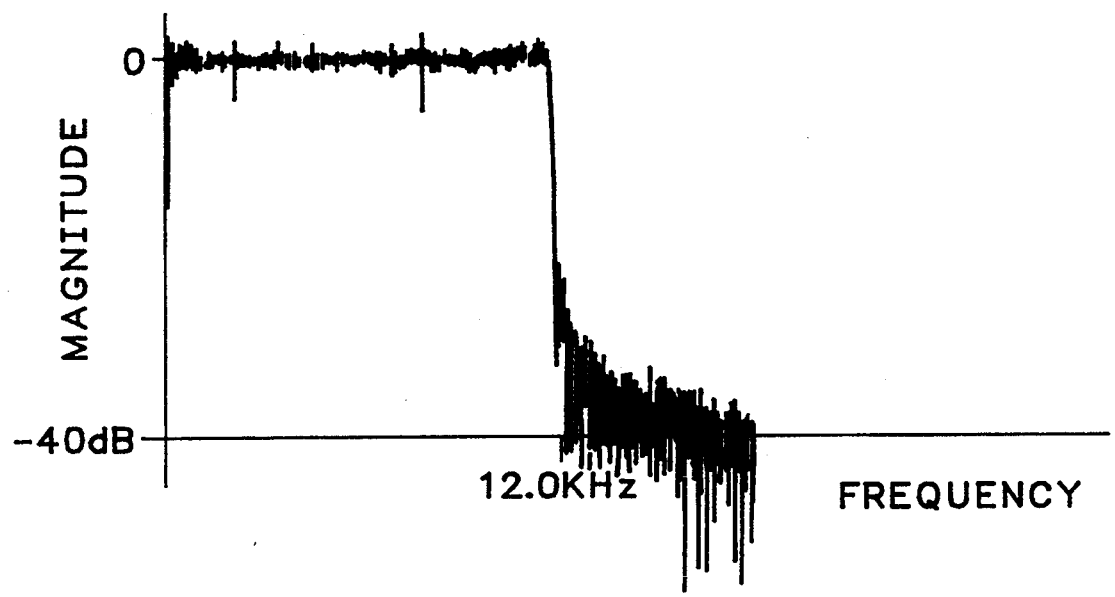
FIG. 45 is an illustration of the effective magnitude response of the recorder and playback unit after application of the correction filter.

FIG. 45 illustrates the effective magnitude response of the recorder and playback unit after application of the FIR correction filter. The magnitude is now flat within the desired frequency band. The magnitude response outside the desired frequency band (e.g. frequencies greater than 100 Hz) is significantly attenuated to remove high frequency noise.

Figure 46:
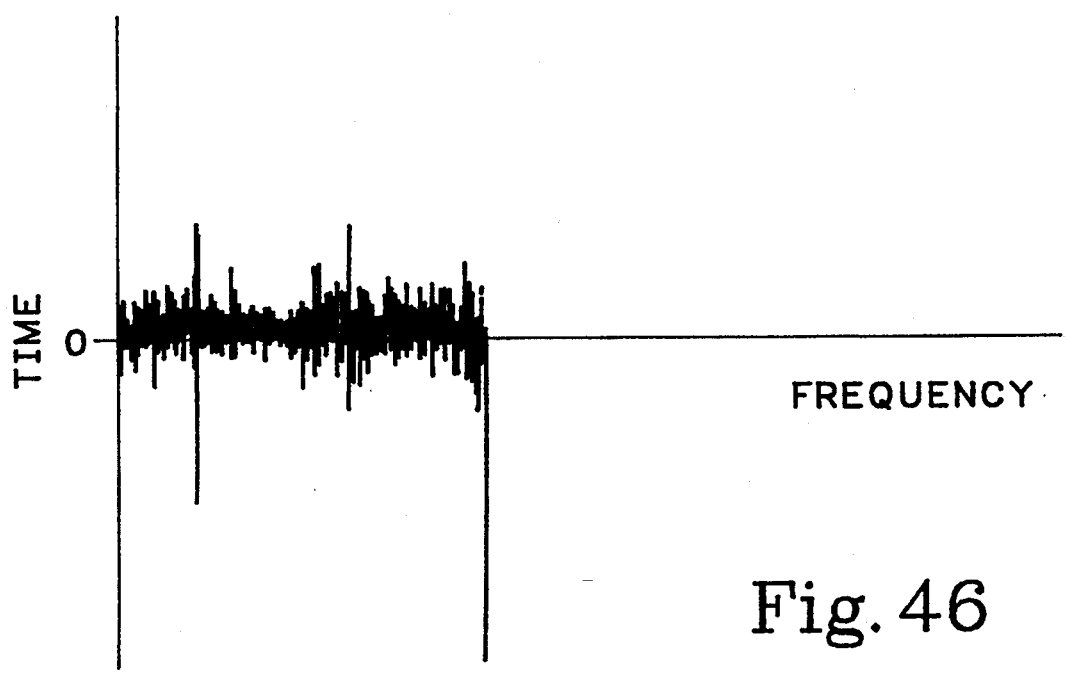
FIG. 46 is an illustration of the group delay of the recorder and playback unit after application of the correction filter.

FIG. 46 illustrates the group delay for the recorder and playback unit after application of the correction filter. The group delay at frequencies within the desired frequency band remain constant indicating a linear phase response. Thus, application of the correction filter to ECG data increase the effective bandwidth of the recorder and playback unit.

It should be appreciated that all of the above described digital signal processing can be implemented by a computer program which can be run on the system illustrated in FIG. 1. Such a program can be written based on the above description by a person having ordinary skill in the art of designing, implementing and using digital filters. Each time the playback unit is used to play back data from a Holter tape, a correction filter as described above can be implemented. This creates a new filter which responds to and corrects for changing parameters such as tape type, head wear in both the recorder and playback unit, and the type of recorder used to record the ECG data.

13. Measuring Recorder and Playback Performance

In analog tape ECG recordings, it is difficult to determine when a recorder or playback unit no longer performs to an acceptable level in terms of its frequency response and time base variation. Changes in the front end circuitry and head wear through age or environment will cause frequency response distortions and the wearing out of moving parts decrease the time base stability of the recorder and playback unit.

By analyzing the recorder and playback signal response, more in-depth testing of system performance is carded out. If the signal response indicates the system is not correctly calibrated, the recorder and/or playback unit can be serviced before starting another ECG recording session. The recorder and playback output characterization signal can be used to measure and record the performance of the recorder and the playback unit each time they are used or on a periodic maintenance period.

In addition to correcting distortion occurring during the recording and playback process, the filter parameters can be compared against a preselected filter standard. When the current parameters vary by a predetermined amount, an alert can be generated to signal that the system be checked to determine whether maintenance or other service is required.

Having described and illustrated the principles of the invention in a preferred embodiment thereof, it is apparent to those skilled in the art that the invention can be modified in arrangement and detail without departing from such principles. I therefore claim all modifications and variation coming within the spirit and scope of the following claims.

We claim:

1. A method for obtaining corrected ECG data in a system comprising a recorder and a playback unit, said method comprising the steps of:
   dynamically measuring a system frequency response of said system;
   deriving a correction filter response from the system frequency response and a predetermined desired response;
   recording ECG data with said recorder, thereby creating recorded ECG data;
   filtering said recorded ECG data according to the correction filter response, thereby creating said corrected ECG data; and outputting said corrected ECG data.

2. The method of claim 1, wherein said step of dynamically measuring a system frequency response further comprises the steps of:
   generating an input characterization signal;
   recording said input characterization signal, thereby creating a recorded characterization signal;
   playing back the recorded characterization signal, thereby creating an output characterization signal; and
   generating said system frequency response from the input characterization signal and the output characterization signal.

3. The method of claim 2 wherein said method further comprises the step of integrating the output characterization signal to compensate for a differentiation effect produced by said playback unit.

4. The method of claim 3, wherein the step of integrating the output characterization signal further comprises the steps of:
   forward filtering the recorded ECG data to provide a first data set in a forward time sequence;
   reversing the order of the first data set;
   reverse filtering the first data set to provide a second data set in a reverse time sequence; and
   reversing the order of the second data set to provide an integrated output data set with a linear phase response.

5. The method of claim 2 wherein said step of generating said input characterization signal further comprises the step of:
   interleaving calibration pulses with an impulse signal to obtain the input characterization signal;
said method further comprising the step of:
   using said calibration pulses to scale the recorded ECG data to more correctly represent said ECG data.

6. The method of claim 1, wherein said step of dynamically measuring a system frequency response comprises the steps of:
   generating a plurality of input characterization signals;
   recording and playing back each of said plurality of input characterization signals to generate a corresponding plurality of output characterization signals;
   averaging said plurality of output characterization signals to obtain an average output characterization signal; and
   generating the system frequency response from one of said input characterization signals and the average output characterization signal.

7. The method of claim 1 wherein said method further comprises the step of integrating the ECG data to compensate for a differentiation effect produced by said playback unit.

8. The method of claim 7, further comprising the step of:
   simultaneously performing said step of integrating said ECG data and filtering said recorded ECG data.

9. The method of claim 1, wherein said step of dynamically measuring a system frequency response comprises the steps of:
   generating a plurality of input characterization signals;
   recording and playing back each of said plurality of input characterization signals to generate a corresponding plurality of output characterization signals;
   statistically selecting a subset of said corresponding plurality of output characterization signals;
   averaging said subset of said corresponding plurality of output characterization signals to obtain an average output characterization signal; and
   generating the system frequency response from one of said input characterization signals and the average output characterization signal.

10. The method of claim 1 further comprising the steps of:
    recording new ECG data with said recorder, thereby creating new recorded ECG data;
    deriving an updated correction filter response from one of said input characterization signals, the average output characterization signal, and said predetermined desired response; and
    filtering the new ECG data with the updated correction filter response.

11. An ECG recorder and playback system for obtaining corrected ECG data, comprising:
    means for dynamically measuring a system frequency response of said system;
    means for deriving a correction filter response from the system frequency response and a predetermined desired response;
    means for recording ECG data with said recorder, thereby creating recorded ECG data;
    means for filtering said recorded ECG data according to the correction filter response, thereby creating said corrected ECG data; and
    means for outputting said corrected ECG data.

12. The system of claim 11, wherein the system further comprises means for selectively boosting the amplitude of the ECG data and the amplitude of the input characterization signal within a predetermined frequency range prior to recording.

13. The system of claim 11, wherein said means for dynamically measuring a system frequency response further comprises:
   means for generating an input characterization signal;
   means for recording said input characterization signal, thereby creating a recorded characterization signal;
   means for playing back the recorded characterization signal, thereby creating an output characterization signal; and
   means for generating said system frequency response from the input characterization signal and the output characterization signal.

14. The system of claim 13, wherein the input characterization signal comprises a repetitive impulse signal.

15. The system of claim 13, wherein the input characterization signal comprises calibration pulses, said system further comprising:
   means for using said calibration pulses to scale the recorded ECG data to more correctly represent said ECG data.

16. The system of claim 15, wherein the input characterization signal comprises an impulse signal interleaved between said calibration pulses.

17. The system of claim 16 wherein the system transfer function generating means further comprises means for extracting the impulse signal from the input characterization signal.

18. The system of claim 13, wherein said input characterization signal further comprises noise, said means for dynamically measuring a system frequency response of said system further comprising:
   means for reducing said noise in said output characterization signal.

19. The system of claim 18 wherein the noise reduction means comprises:
   means for using a phase ramp on unaligned pulses in the frequency domain of the output characterization signal to a predetermined reference point, thereby creating a plurality of aligned pulses;
   means for accumulating said plurality of aligned pulses;
   means for averaging the accumulated aligned pulses to create a composite characterization signal; and
   means for generating said system frequency response from said input characterization signal and said composite characterization signal.

20. The system of claim 11, further comprising:
   means for integrating the ECG patient and characterization signals to compensate for a differentiation effect produced by said system.

21. The system of claim 20, wherein the means for integrating the output characterization signal further comprises:
   a first filter for forward filtering the recorded EGG data to provide a first data set in a forward time sequence;
   means for reversing the order of the first data set;
   a second filter for reverse filtering the first data set to provide a second data set in a reverse time sequence; and
   means for reversing the order of the second data set to provide an integrated output data set with a linear phase response.

22. The system of claim 21, wherein said first filter is a high pass filter.

23. The system of claim 21, wherein said second filter is a low pass filter.

24. The system of claim 21, wherein said second filter is a band pass filter.

25. The system of claim 11, wherein said means for outputting said corrected ECG data is a printer.

26. The system of claim 11, wherein said means for outputting said corrected ECG data is a display.

27. A system for obtaining corrected ECG data, comprising:
   an ECG recorder for recording ECG data, thereby creating recorded ECG data;
   a playback unit, comprising:
      a playback transport having an output for playing back said recorded ECG data;
      an amplifier having an input coupled to the output of the playback transport and an output for providing amplified ECG data;
      a correction filter having an input coupled to the amplifier output, an output for providing corrected ECG data, said correction filter responsive to a dynamically measured system frequency response of said system and a predetermined desired response of said system; and
   a printer for printing said corrected ECG data.

28. The system of claim 27, wherein the correction filter has a transfer function created to be the inverse of a transfer function for the system.

29. The system of claim 27, further comprising means for integrating the recorded ECG data to compensate for a differentiation effect produced by said playback unit.

30. The system of claim 29, wherein the means for integrating the recorded ECG data further comprises:
   a first filter for forward filtering the recorded ECG data to provide a first data set in a forward time sequence;
   means for reversing the order of the first data set;
   a second filter for reverse filtering the first data set to provide a second data set in a reverse time sequence; and
   means for reversing the order of the second data set to provide an integrated output data set with a linear phase response.

31. The system of claim 30, wherein said first filter is a high pass filter.

32. The system of claim 30, wherein said second filter is a low pass filter.

33. The system of claim 30, wherein said second filter is a bandpass filter.

* * * * *